United States Patent
Zellner

(10) Patent No.: US 12,020,182 B2
(45) Date of Patent: *Jun. 25, 2024

(54) VENUE SEAT ASSIGNMENT BASED UPON HEARING PROFILES

(71) Applicant: AT&T Intellectual Property I, L.P., Atlanta, GA (US)

(72) Inventor: Samuel N. Zellner, Atlanta, GA (US)

(73) Assignee: AT&T Intellectual Property I, L.P., Atlanta, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/831,620

(22) Filed: Jun. 3, 2022

(65) Prior Publication Data

US 2022/0292410 A1    Sep. 15, 2022

Related U.S. Application Data

(63) Continuation of application No. 16/264,064, filed on Jan. 31, 2019, now Pat. No. 11,354,604.

(51) Int. Cl.
G06Q 10/02    (2012.01)
A61B 5/12     (2006.01)
H04W 4/021    (2018.01)

(52) U.S. Cl.
CPC ........... G06Q 10/02 (2013.01); A61B 5/121 (2013.01); H04W 4/021 (2013.01)

(58) Field of Classification Search
CPC .................. G06Q 10/02; A61B 5/121
See application file for complete search history.

(56) References Cited

U.S. PATENT DOCUMENTS 7,529,545 B2    5/2009    Rader et al.
7,936,885 B2    5/2011    Frank et al.
(Continued)

FOREIGN PATENT DOCUMENTS

GB    2536093       8/2017
JP    2007026328    2/2007
(Continued)

OTHER PUBLICATIONS

Toole, Floyd. "The measurement and calibration of sound reproducing systems." Journal of the Audio Engineering Society 63.7/8 (2015): 512-541. (Year: 2015).*

(Continued)

*Primary Examiner* — Scott M Tungate
(74) *Attorney, Agent, or Firm* — Hartman & Citrin LLC

(57) ABSTRACT

The concepts and technologies disclosed herein are directed to venue seat assignment based upon hearing profiles. According to one aspect of the concepts and technologies disclosed herein, a device can include a processor and a memory. The device can receive a request to upload a hearing profile, and can upload the hearing profile to a seat assignment system. The device can receive, from the seat assignment system, a customized seating chart based, at least in part, upon the hearing profile. The customized seating chart can include a visual representation of at least a portion of seating in a venue. The device can select, from the customized seating chart, a seat from the portion of the seating in the venue. This selection can be made automatically or based upon user input.

20 Claims, 23 Drawing Sheets

(56) References Cited

U.S. PATENT DOCUMENTS

| | | | |
|---|---|---|---|
| 8,050,419 B2 | 11/2011 | Gerlach | |
| 8,081,765 B2 | 12/2011 | Yu | |
| 8,964,998 B1* | 2/2015 | McClain | H03G 3/32 |
| | | | 381/106 |
| 9,025,783 B2 | 5/2015 | Mahowald | |
| 9,344,815 B2 | 5/2016 | Selig et al. | |
| 9,468,401 B2 | 10/2016 | Van Hasselt et al. | |
| 9,525,392 B2 | 12/2016 | Krishnaswamy | |
| 9,548,713 B2 | 1/2017 | Wang et al. | |
| 9,641,660 B2 | 5/2017 | Kim | |
| 9,743,212 B2 | 8/2017 | Ridihalgh et al. | |
| 9,794,672 B2 | 10/2017 | Campbell et al. | |
| 9,943,253 B2 | 4/2018 | Raz | |
| 9,948,256 B1 | 4/2018 | Dow et al. | |
| 9,980,076 B1* | 5/2018 | Pratt | H04S 7/303 |
| 9,990,171 B2 | 6/2018 | Yang et al. | |
| 2004/0049125 A1* | 3/2004 | Nakamura | A61B 5/0002 |
| | | | 600/559 |
| 2008/0153537 A1 | 6/2008 | Khawand et al. | |
| 2008/0298614 A1 | 12/2008 | Cronin et al. | |
| 2010/0150359 A1* | 6/2010 | KnicKrehm | G09B 23/14 |
| | | | 381/71.7 |
| 2010/0329490 A1 | 12/2010 | Van Schijndel et al. | |
| 2011/0095875 A1 | 4/2011 | Thyssen et al. | |
| 2014/0309549 A1* | 10/2014 | Selig | A61B 5/123 |
| | | | 600/559 |
| 2014/0334644 A1 | 11/2014 | Selig et al. | |
| 2016/0149547 A1 | 5/2016 | Rider et al. | |
| 2016/0301375 A1 | 10/2016 | Watts | |
| 2018/0012589 A1 | 1/2018 | MacNeille et al. | |
| 2018/0249263 A1 | 8/2018 | Raz et al. | |
| 2020/0296523 A1* | 9/2020 | Von Brasch | H04R 25/43 |

FOREIGN PATENT DOCUMENTS

| | | |
|---|---|---|
| NL | 1040893 | 9/2016 |
| WO | WO 2016/020908 | 2/2016 |

OTHER PUBLICATIONS

Von Klitzing, Tim, "'Earprint' or the introduction to personalized sound," medium.com, Nov. 16, 2016.
"A-01 Headphones," Audeara, audeara.com, Nov. 29, 2018.
S. Figueira, K. Nguyen, and S. Panditrao, "HearThat?—An app for diagnosing hearing loss," IEEE Global Humanitarian Technology Conference (GHTC 2014), San Jose, CA, 2014, pp. 518-524, doi: 10.1109/GHTC.2014.6970332. (Year: 2014).
U.S. Office Action dated Sep. 16, 2020 in U.S. Appl. No. 16/264,064.
U.S. Office Action dated Jan. 21, 2021 in U.S. Appl. No. 16/264,064.
U.S. Office Action dated May 7, 2021 in U.S. Appl. No. 16/264,064.
U.S. Office Action dated Oct. 13, 2021 in U.S. Appl. No. 16/264,064.
U.S. Notice of Allowance dated Jan. 26, 2022 in U.S. Appl. No. 16/264,064.

* cited by examiner

VENUE SEAT ASSIGNMENT BASED UPON HEARING PROFILES

CROSS-REFERENCE TO RELATED APPLICATIONS

This application is a continuation of and claims priority to U.S. patent application Ser. No. 16/264,064, entitled "Venue Seat Assignment Based Upon Hearing Profiles," filed Jan. 31, 2019, now U.S. Pat. No. 11,354,604, which is incorporated herein by reference in its entirety.

BACKGROUND

Audio content producers intend their content to be heard in a specific way. It may be very difficult, however, for their efforts to account for the numerous source devices that can be used to playback their audio content, in addition to the speakers/headphones used, environment acoustics, and, perhaps most difficult, the hearing abilities of the listener(s). Equalizers allow listeners to customize audio playback to suit their listening preferences. This is typically a manual process and can require adjustment depending on the specific audio content, audio playback system, speakers/headphones, and the environment.

SUMMARY

Concepts and technologies disclosed herein are directed to venue seat assignment based upon hearing profiles. According to one aspect of the concepts and technologies disclosed herein, a device can include a processor and a memory. The device can receive a request to upload a hearing profile. The device can upload the hearing profile to a seat assignment system. The device can receive, from the seat assignment system, a customized seating chart based, at least in part, upon the hearing profile. The customized seating chart can include a visual representation of at least a portion of seating in a venue. The device can select, from the customized seating chart, a seat from the portion of the seating in the customized seating chart. This selection can be made automatically, or manually based upon user input.

In some embodiments, the device also can include a display. The device can present, on the display, a graphical user interface ("GUI") that shows an upload hearing profile option. In these embodiments, the device can receive the request to upload the hearing profile responsive to the upload hearing profile option being selected. The device also can identify from where the hearing profile should be uploaded. In some embodiments, the device can designate a hearing profile stored in the memory of the device. Alternatively, the device can designate a hearing profile associated with a hearing test application.

In some embodiments, the device can automatically select, from the customized seating chart, the seat from the portion of the seating in the customized seating chart. In particular, the device can receive selection of an automatic seat selection option and can automatically select the seat from the portion of the seating in the venue. In other embodiments, the device can select, from the customized seating chart, the seat from the portion of the seating in the venue in response to a user input.

It should be appreciated that the above-described subject matter may be implemented as a computer-controlled apparatus, a computer process, a computing system, or as an article of manufacture such as a computer-readable storage medium. These and various other features will be apparent from a reading of the following Detailed Description and a review of the associated drawings.

This Summary is provided to introduce a selection of concepts in a simplified form that are further described below in the Detailed Description. This Summary is not intended to identify key features or essential features of the claimed subject matter, nor is it intended that this Summary be used to limit the scope of the claimed subject matter. Furthermore, the claimed subject matter is not limited to implementations that solve any or all disadvantages noted in any part of this disclosure.

DETAILED DESCRIPTION

Figure 1:
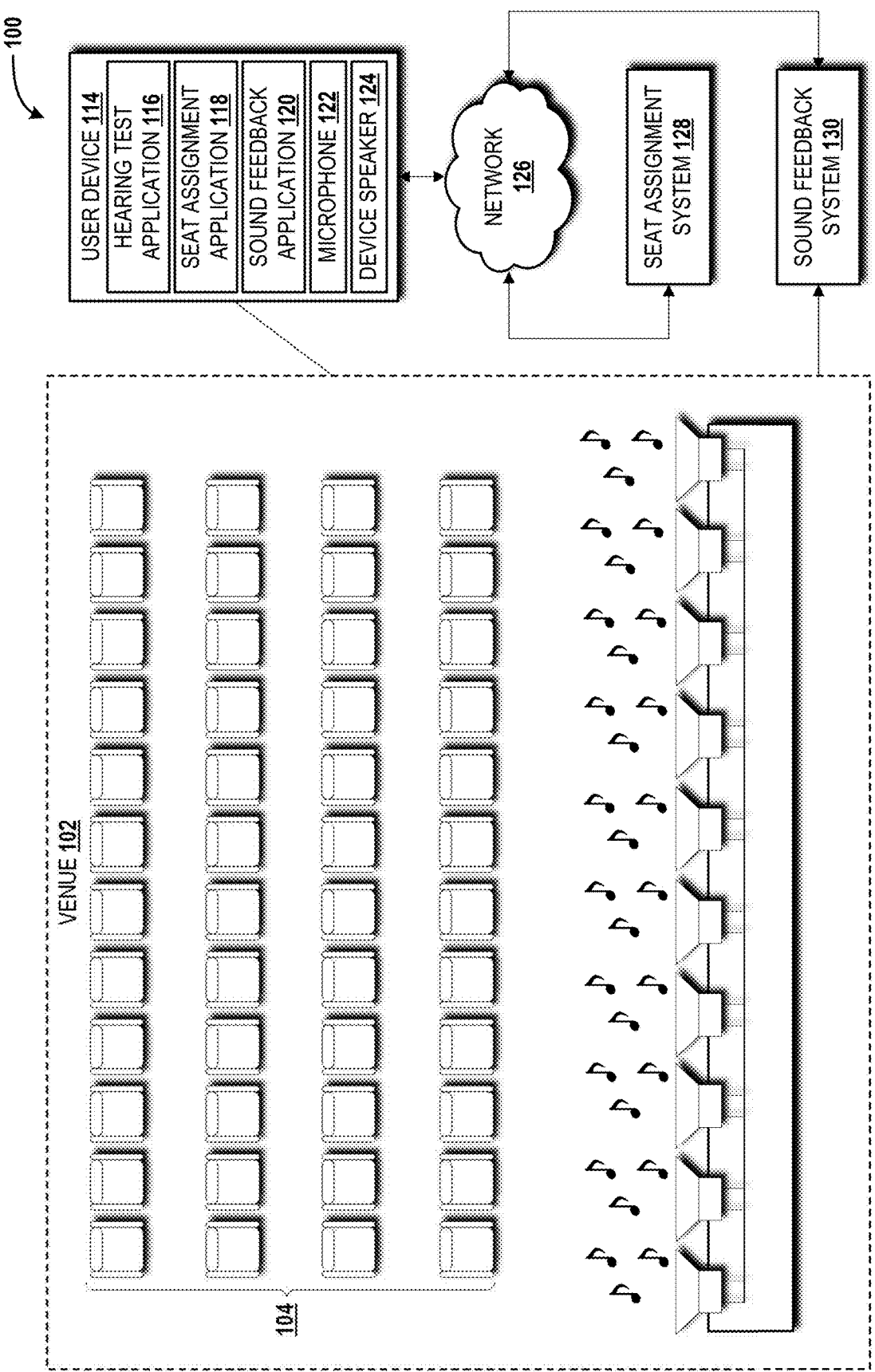
FIG. 1 is a block diagram illustrating aspects of an illustrative operating environment for various concepts disclosed herein.

While the subject matter described herein may be presented, at times, in the general context of program modules that execute in conjunction with the execution of an operating system and application programs on a computer system, those skilled in the art will recognize that other implementations may be performed in combination with other types of program modules. Generally, program modules include routines, programs, components, data structures, computer-executable instructions, and/or other types of structures that perform particular tasks or implement particular abstract data types. Moreover, those skilled in the art will appreciate that the subject matter described herein may be practiced with other computer systems, including handheld devices, vehicles, wireless devices, multiprocessor systems, distributed computing systems, microprocessor-based or programmable consumer electronics, minicomputers, mainframe computers, routers, switches, other computing devices described herein, and the like.

In the following detailed description, references are made to the accompanying drawings that form a part hereof, and in which are shown by way of illustration specific embodiments or examples. Referring now to the drawings, in which like numerals represent like elements throughout the several figures, aspects of the concepts and technologies disclosed herein for venue seat assignment based upon hearing profiles will be described.

Referring now to FIG. 1, aspects of an illustrative operating environment 100 for various concepts disclosed herein will be described. It should be understood that the operating environment 100 and the various components thereof have been greatly simplified for purposes of description. Accordingly, additional or alternative components of the operating environment 100 can be made available without departing from the embodiments described herein.

The illustrated operating environment 100 includes a venue 102 that provides seating 104 for a plurality of users 106A-106I (hereinafter referred to collectively as "users 106" or individually as a "user 106"). The venue 102 can be any place and is not limited to specific venue types. By way of example, and not limitation, the venue 102 might be a theater, a stadium, a lecture hall, a classroom, a music venue, an outdoor venue, an indoor venue, or the like. Moreover, the venue 102 can include a private venue, such as a person's home (e.g., home theater room), or even a vehicle. The illustrated venue 102 includes a venue audio system 108 that provides audio output 110 via one or more speakers 112 to be heard by at least a portion of the users 106.

The venue audio system 108 can include any number of audio input sources, such as, for example, microphones, preamplifiers and/or other direct interfaces, and line sources. The venue audio system 108 can include any number of amplifiers, mixing consoles, monitors (including in-ear monitors), and the like. The venue audio system 108 can be chosen for an application, such as a movie theater versus a stadium or live concert venue. Those skilled in the art will appreciate the near limitless combinations of audio equipment that can be implemented as the venue audio system 108 to provide audio for a given venue 102. For example, an implementation of the venue audio system 108 for a movie theater is likely different from an implementation of the venue audio system 108 for a live concert venue. As such, the examples provided herein should not be construed as being limiting in any way.

The speakers 112 can include any number of speakers. The speakers 112 can include active speakers, passive speakers, or a combination thereof. The speakers 112 can utilize any driver design, some examples of which include full-range, mid-range, subwoofer, tweeter, and the like. The speakers 112 can be housed in any enclosure type. The speakers 112 can connect to the venue audio system 108 via any wired or wireless connection. Two or more of the speakers 112 can be connected in a similar manner. The specification of the speakers 112 can be selected to suit the needs of a given implementation in the venue 102. The materials used to design the speakers 112 and other characteristics of the speakers 112 can be likewise selected. The speakers 112, in some embodiments, can form at least one speaker array (e.g., a line array of the speakers 112, a surround sound system formed by the speakers 112, or the like). In some embodiments, the speakers 112 are designed to form a sound field from the audio output 110. The sound field can be created, at least in part, by the venue audio system 108, to simulate certain sound stages, including speaker virtualization and other advanced digital signal processing techniques. The sound field, in some embodiments, might include multiple sub-fields that might utilize audio beamforming to direct the audio output 110 to specific users 106. In this manner, the venue audio system 108 can control the properties of the audio output 110 to different users 106 in the venue 102. In some embodiments, the properties are modified based, at least in part, upon an individual hearing profile of at least one of the users 106 or a group hearing profile of at least two of the users 106. Additional details about hearing profiles are provided below.

The seating 104 can be arranged in any way within the venue 102. Although individual seats are illustrated, benches, sofas, and other furniture that might provide seats for multiple users 106 are contemplated. Moreover, the seating 104 might be defined by areas or sections, such as the case might be at certain venues 102 or for certain events at the venue 102. The illustrated seating 104 includes four rows and twelve columns of individual seats. This example is merely illustrative and should not be construed as being limiting in any way. Those skilled in the art will appreciate that the concepts and technologies disclosed herein are applicable to any type of venue attendance, and are not limited to seated attendance at the venue 102 as shown in the illustrated example. As used herein, the concept of "seating" is intended to encompass a placeholder for the users 106 to occupy some space at or within the venue 102, and can encompass arrangements of the venue 102 that do not include physical seats (e.g., standing room only).

The user 106I (hereinafter referred to as "the user 106") is shown in association with a user device 114. In this context, "in association with" means the user device 114 is in his or her possession, on his or her person, or the like; that the user 106 is an owner of the user device 114 (even if not on his or her person); and any other arrangement that may define this "association." According to various embodiments, the functionality of the user device 114 might be provided by one or more mobile telephones, smartphones, tablet computers, slate computers, smart watches, fitness devices, smart glasses, other wearable devices, mobile media playback devices, set top devices, navigation devices, laptop computers, notebook computers, ultrabook computers, netbook computers, server computers, computers of other form factors, computing devices of other form factors, other computing systems, other computing devices, Internet of Things ("IoT") devices, other unmanaged devices, other managed devices, and/or the like. It should be understood that the functionality of the user device 114 can be provided by a single device, by two or more similar devices, and/or by two or more dissimilar devices. In the illustrated example, the user device 114 includes a hearing test application 116, a seat assignment application 118, a sound feedback application 120, a microphone 122, and a device speaker 124. The user device 114 can include other hardware components, such as one or more processing components, one or more memory components, and one or more networking components. An example of the user device 114 embodied as a mobile device (e.g., a smartphone) is illustrated and described below with reference to FIG. 9.

The hearing test application 116 can facilitate the user 106 to take a hearing test via the user device 114. The hearing test(s) offered by the hearing test application 116 might be or might include a general hearing test, a hearing test tailored to specific types of the audio output 110 (e.g., movie audio versus live concert audio), specific to the venue 102, or specific to event types in general or particular to events that occur at the venue 102. The hearing test(s) offered by the hearing test application 116 can utilize any testing methodology. As another example, a pre-show routine at a specific venue could include emitting certain test sounds/frequencies and the users 106 can indicate what they hear. This test could be used to supplement/replace existing hearing test information. In some cases, the testing methodology might require the use of additional equipment, such as sensors, or even a physical exam by an audiologist. In these cases, the hearing test application 116 might be able to import hearing test results from external equipment, such as the equipment used by the audiologist. Regardless of the source of the test results—such as local tests performed via the user device 114 via execution, by one or more processing components, of the hearing test application 116 to perform one or more hearing tests, or remote tests performed by one or more devices other than the user device 114—the hearing test application 116 can use hearing test results to create a hearing profile of the user 106. The venue audio system 108 can utilize hearing profiles to modify the audio output 110 for the user 106. Additional details in this regard will be provided below.

Figure 10:
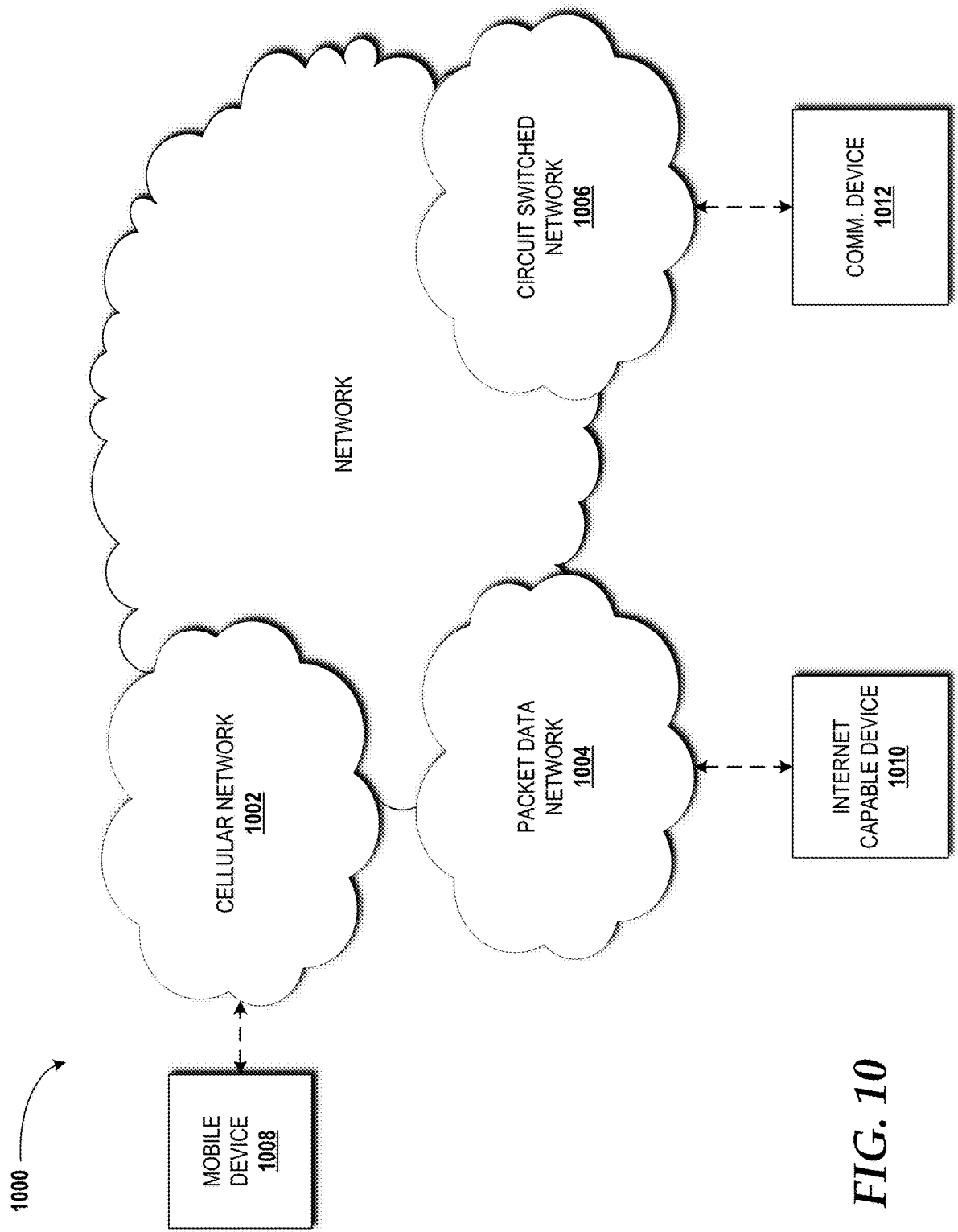
FIG. 10 is a diagram illustrating a network, according to an illustrative embodiment.

The seat assignment application 118 can facilitate the assignment of seats to the users 106 from the seating 104 available in the venue 102. The seat assignment application 118 might provide a visual representation of the seating 104 from which the user 106 can select his or her seat(s) (an example of this is shown in FIG. 2H). The seat assignment application 118 might additionally or alternatively provide an option for the user 106 to upload his or her hearing profile. Based upon the hearing profile of the user 106, the seat assignment application 118 can provide a customized seat recommendation. In some embodiments, the seat assignment application 118 provides a front-end user experience for seat selection and assignment, and communicates, via a network 126 (additional details of which are shown in FIG. 10), with a seat assignment system 128 that conducts the backend processing to determine the customized seat recommendation based upon an uploaded hearing profile.

The sound feedback application 120 can facilitate sound feedback provided by the user 106 while the user 106 is listening to the audio output 110 in the venue 102. The sound feedback can represent any sound characteristics of the audio output 110. In some embodiments, the sound feedback application 120 is designed for the layperson, and as such, allows the user 106 to provide sound feedback such as volume and level feedback (e.g., more or less of the low, mid, and/or high frequencies represented in the audio output 110). In some other embodiments, the sound feedback application 120 is designed for experienced listeners and/or professionals (e.g., audio engineers). The sound feedback application 120 might have different modes that offer varying levels of feedback based upon the knowledge of the user 106. The sound feedback application 120 additionally or alternatively might include an automatic feedback mode that relies, at least in part, upon the audio output 110 as it is received by the microphone 122. The automatic feedback might be based upon known characteristics of the microphone 122 (e.g., one microphone might be better at picking up low frequencies while another might excel at high frequencies), and might take into account the location of the microphone 122, such as in a pocket of a piece of clothing worn by the user 106. By using the automatic feedback mode of the sound feedback application 120, the user 106 can focus on their experience listening to the audio output 110 in the venue 102 instead of manually providing their feedback. The sound feedback, in some embodiments, can be prompted by the sound feedback application 120 via a visible (e.g., via a display of the user device 114) and/or an audible (e.g., via the device speaker 124) prompt.

The sound feedback collected by the sound feedback application 120 can be stored locally on the user device 114 and/or shared by the user device 114 with a sound feedback system 130 via the network 126. In some embodiments, the sound feedback application 120 provides a front-end user experience through which the user 106 can elect to manually or automatically provide sound feedback for the audio output 110, and communicates, via the network 126, with the sound feedback system 130 that collects sound feedback and provides the sound feedback and/or sound adjustment recommendations based upon the sound feedback to the venue audio system 108. In the illustrated example, the sound feedback system 130 is connected to the venue audio system 108, but other implementations can include the sound feedback system 130 being built-in to the venue audio system 108 or networked with the venue audio system 108, such as via the network 126. The venue audio system 108 can adjust the audio output 110 based upon the sound feedback and/or recommendations provided by the sound feedback system 130. The sound feedback system 130 can adjust the audio output 110 over time to optimize the listening experience for the users 106 that visit the venue 102. This can include a continuous refinement of the audio output 110 that carries over from one event at the venue 102 to the next. Alternatively, sound feedback can be particular to a specific event at the venue 102, and any sound feedback collected during that event might be discarded after the event ends.

Figure 2A:
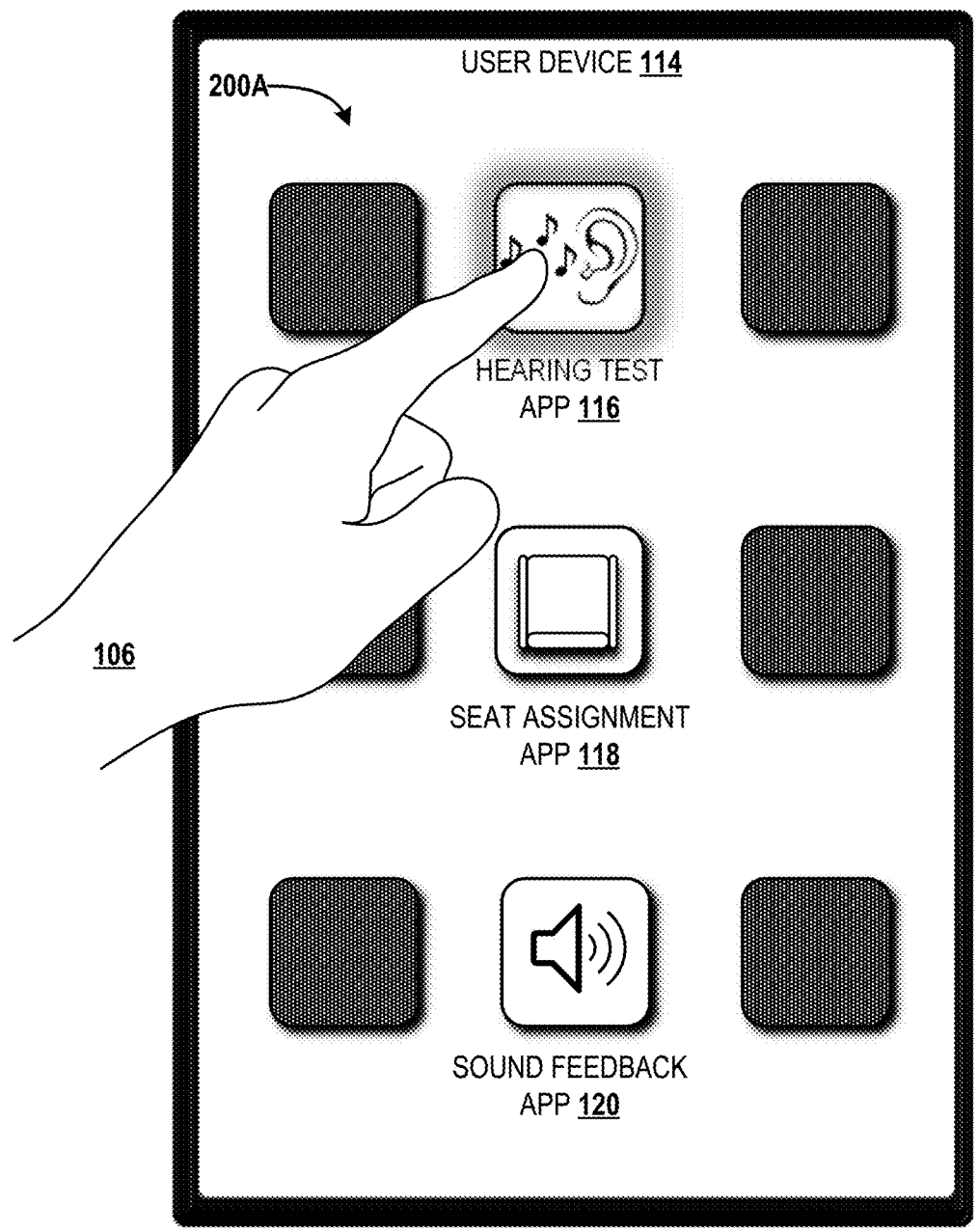
FIGS. 2A-2N are graphical user interface ("GUI") diagrams illustrating aspects of exemplary user interfaces, according to illustrative embodiments of the concepts and technologies disclosed herein.
Figure 2B:
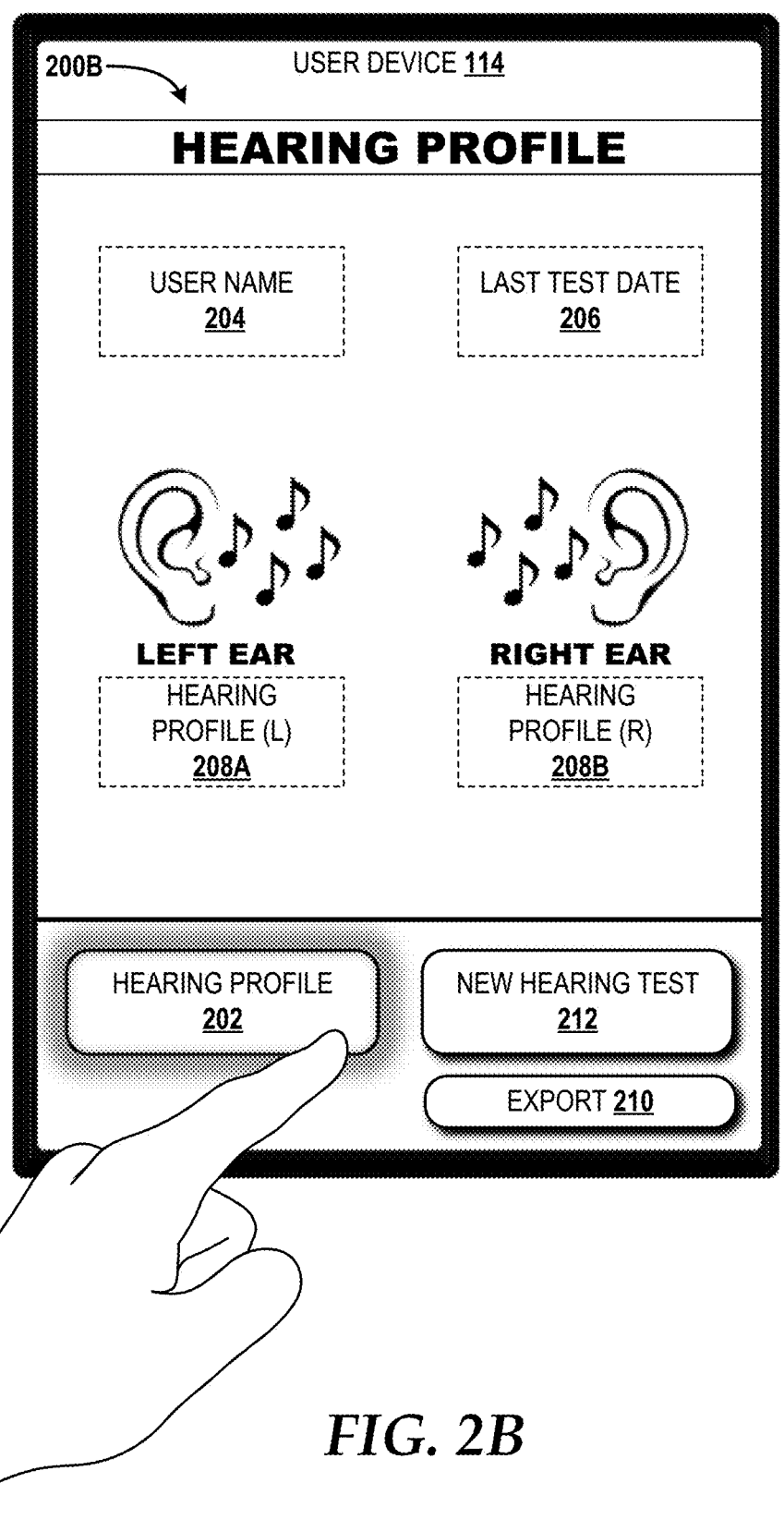
Figure 2C:
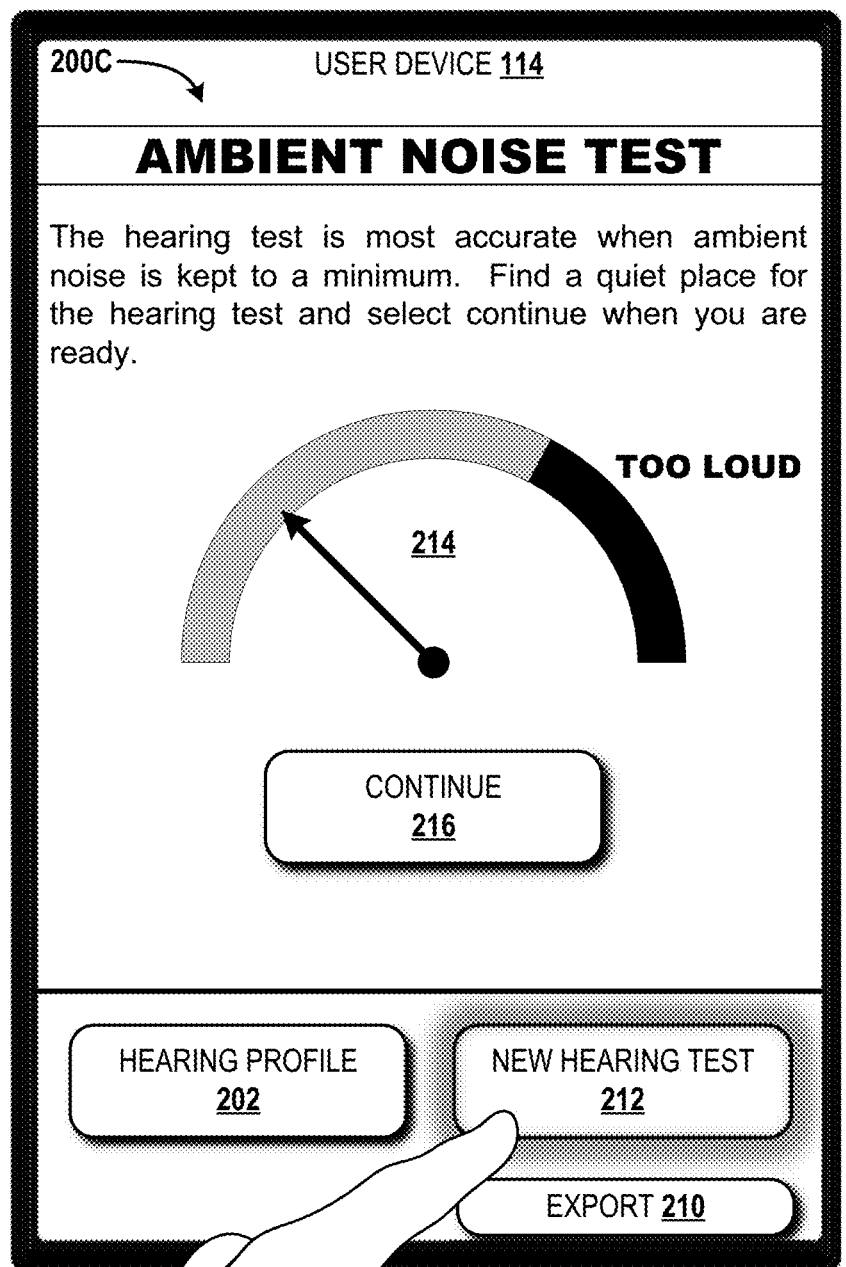
Figure 2D:
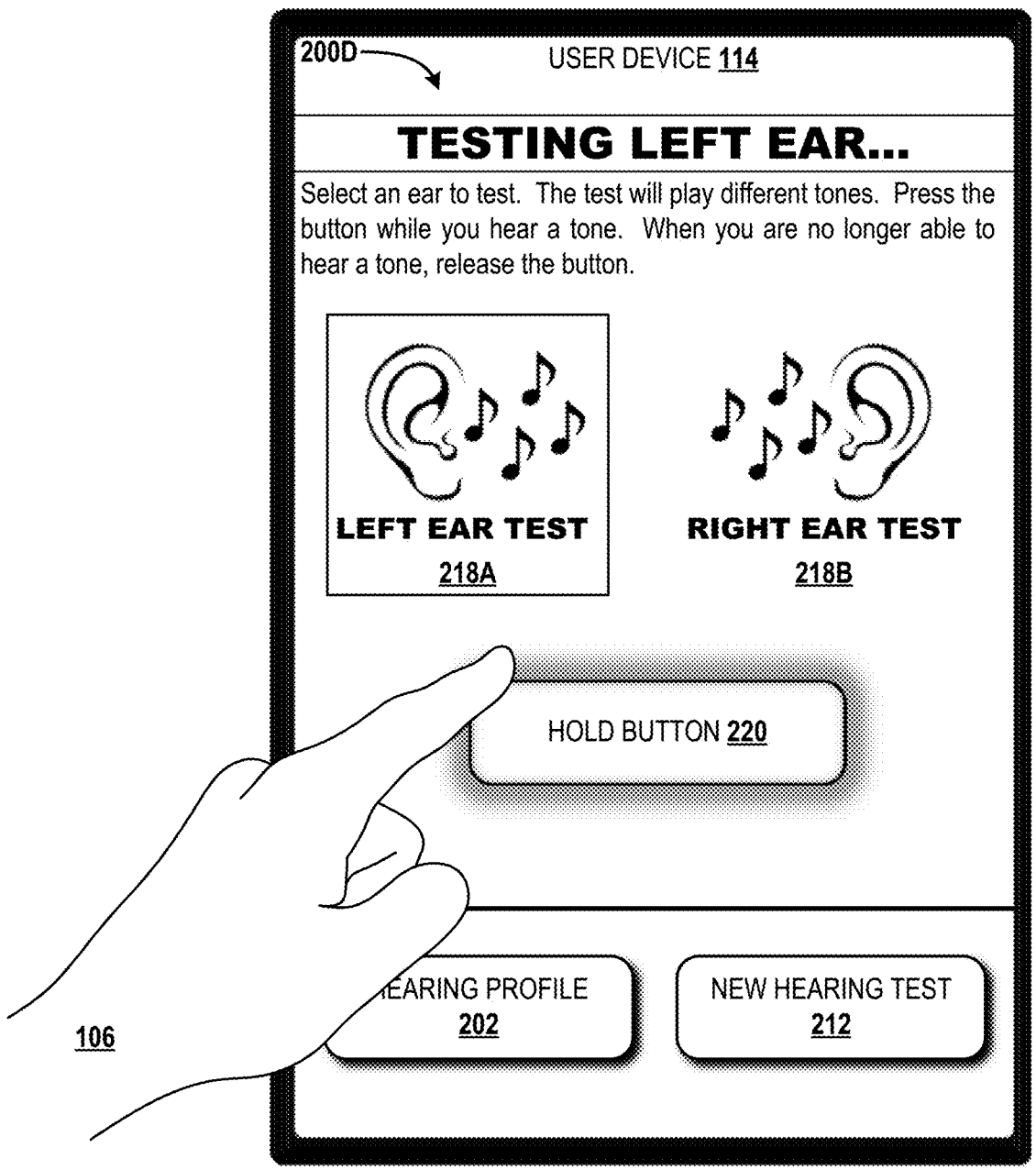
Figure 2E:
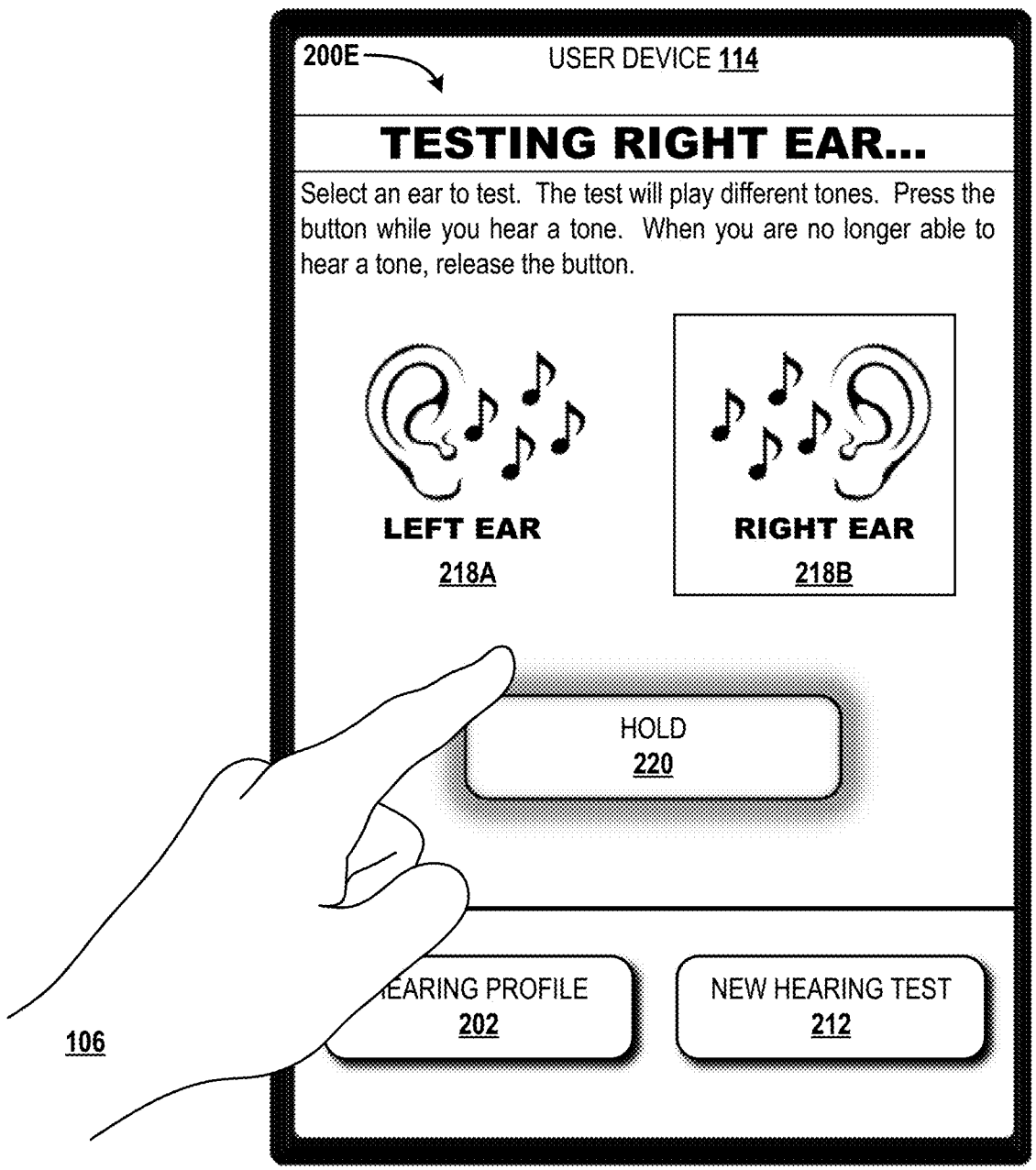
Figure 2F:
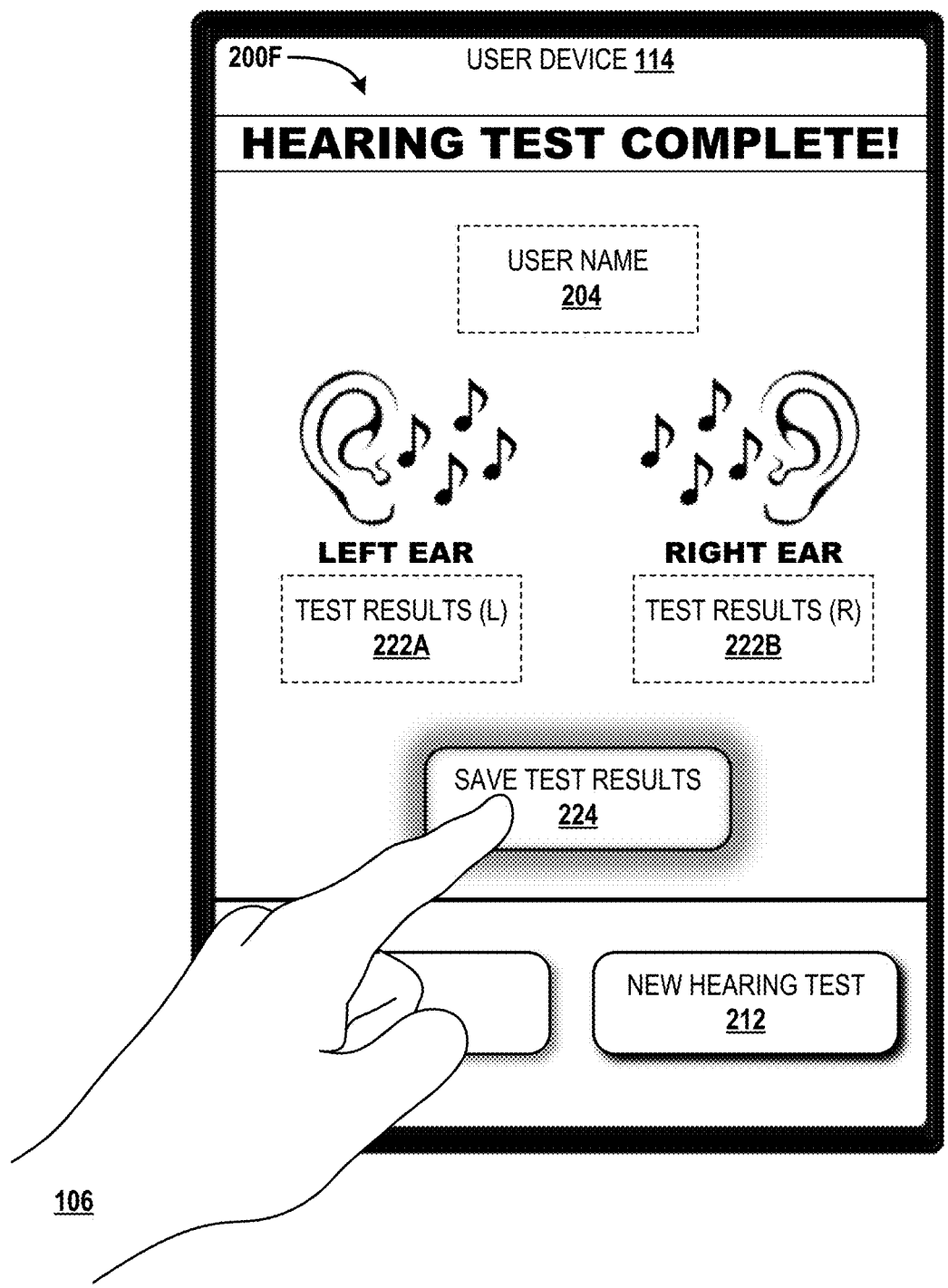
Figure 2G:
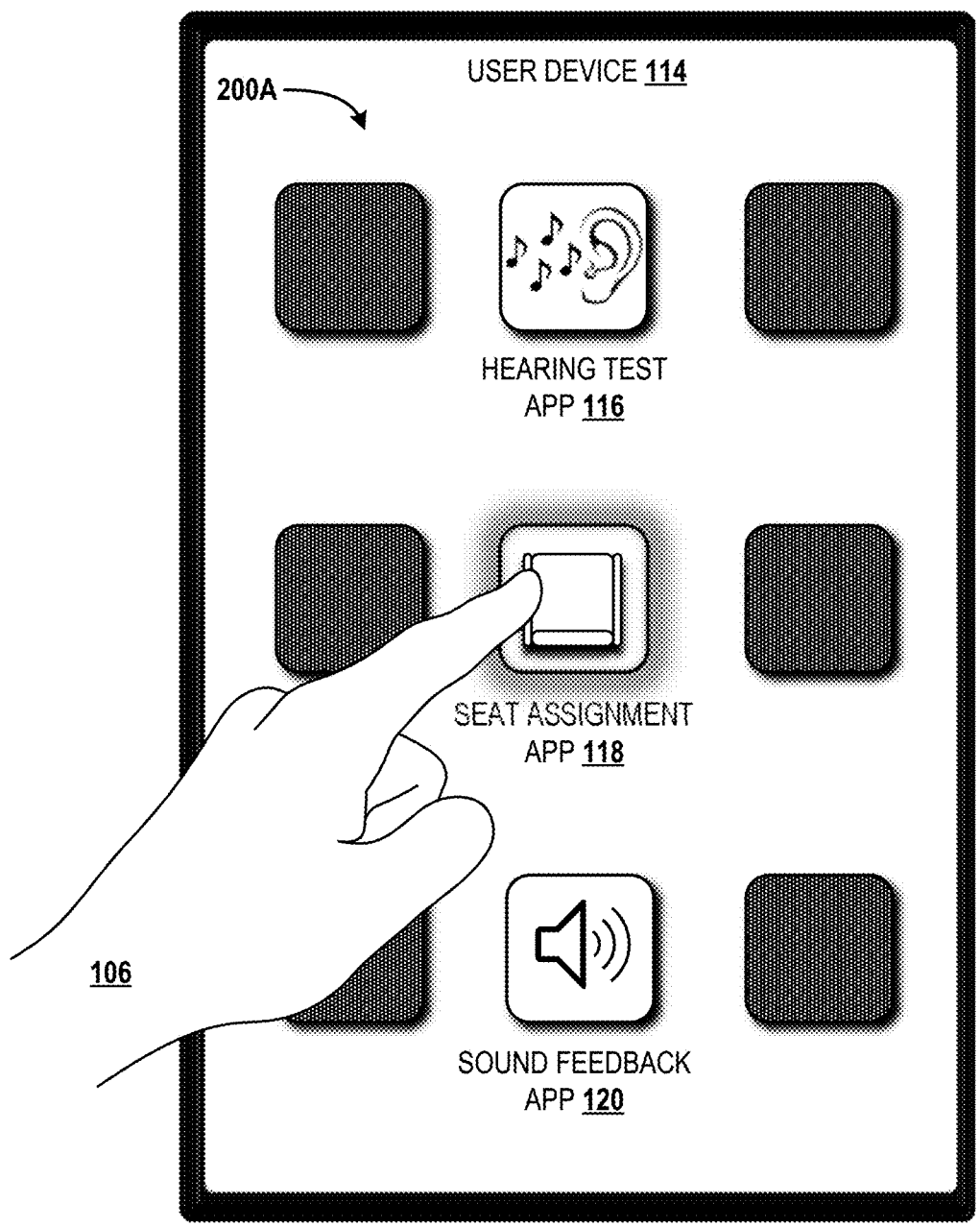
Figure 2H:
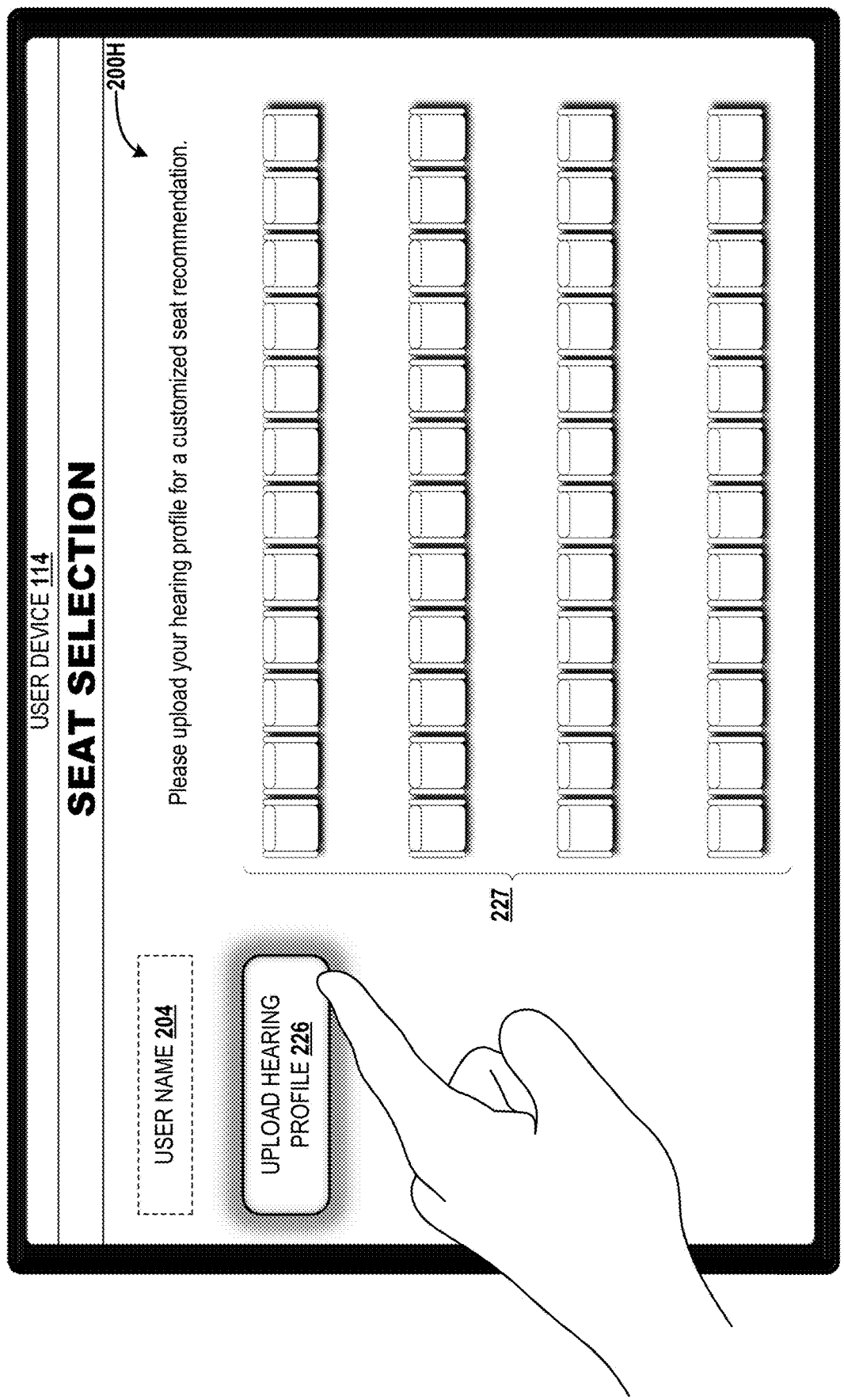
Figure 2I:
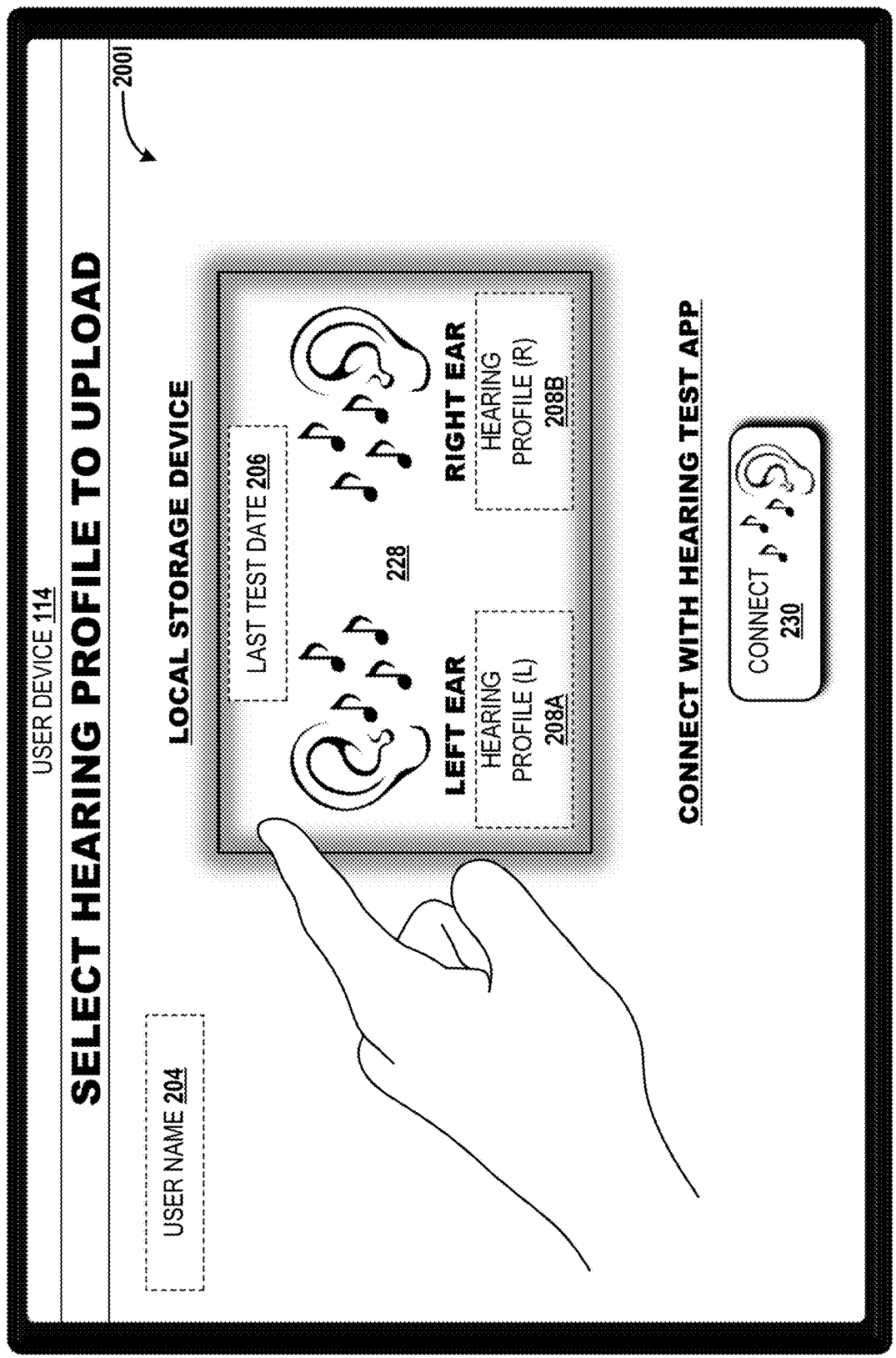
Figure 2J:
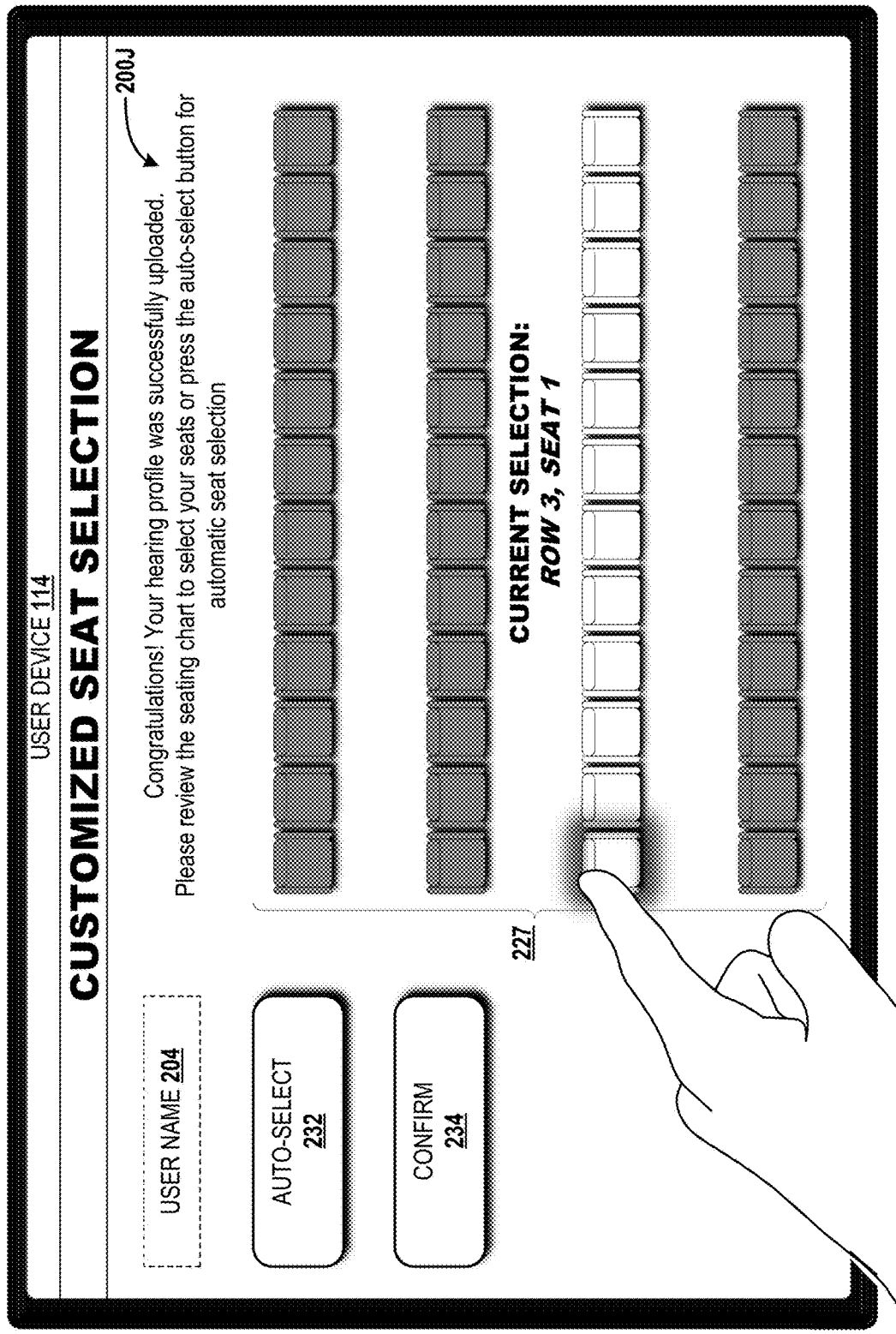
Figure 2K:
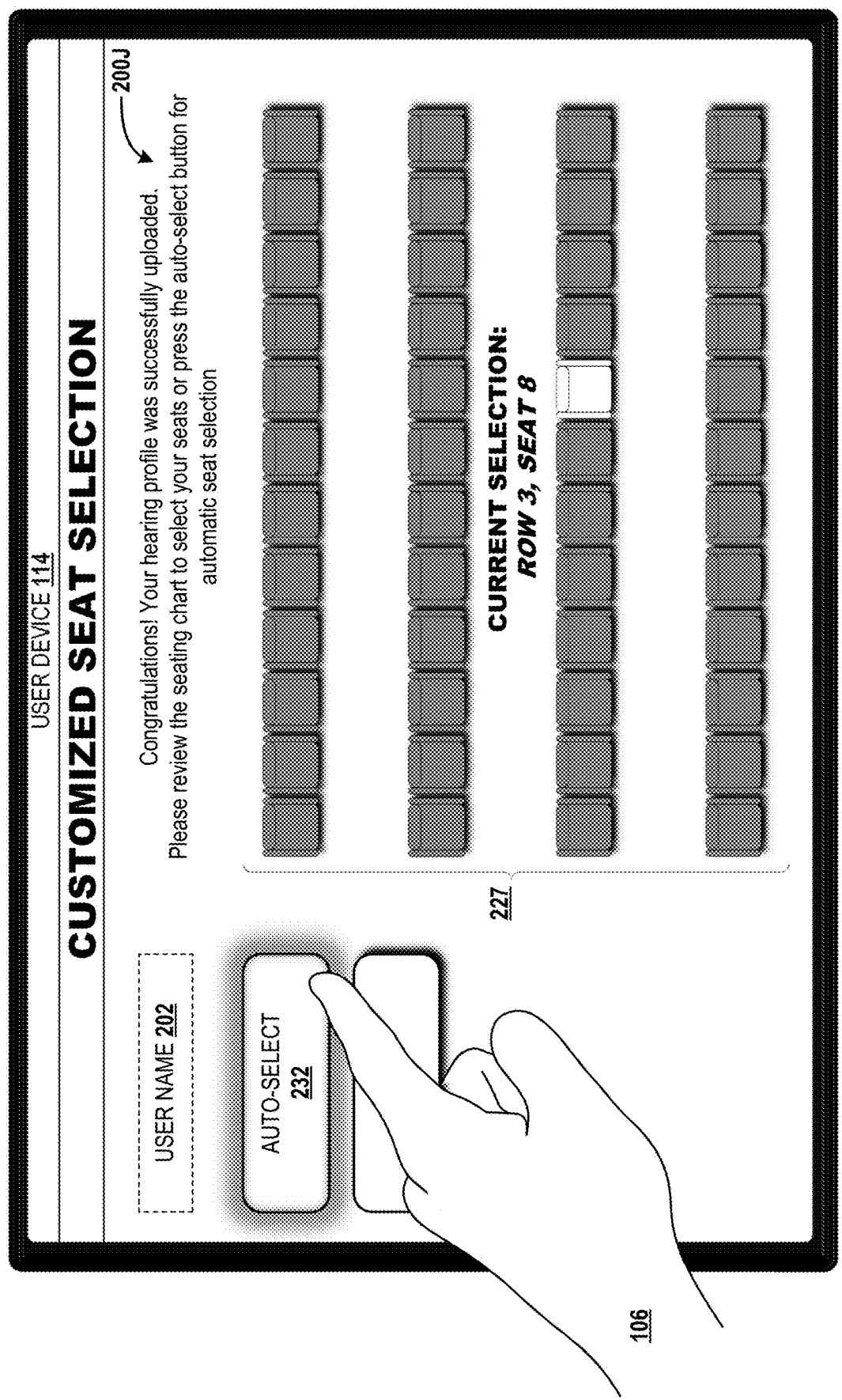
Figure 2L:
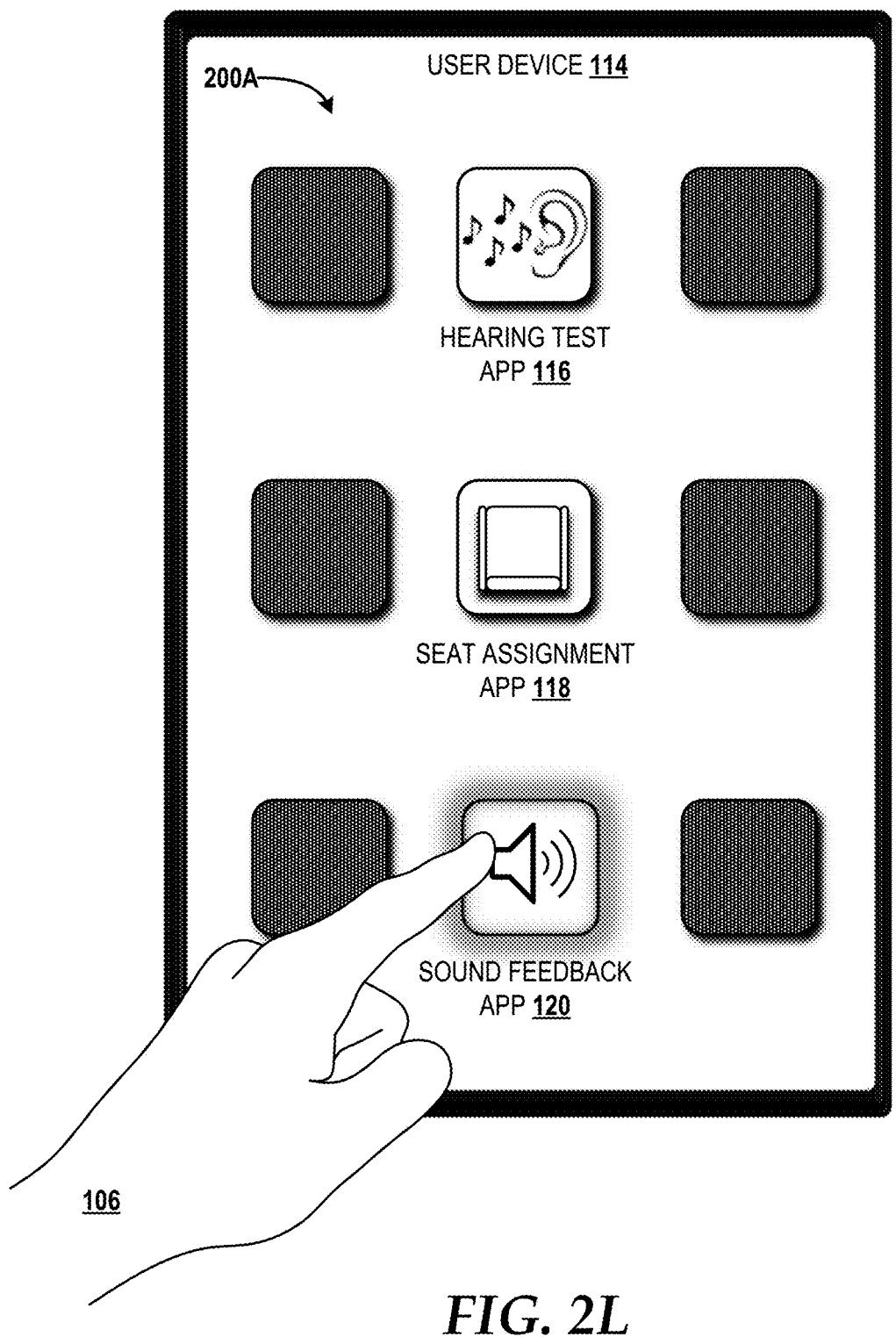
Figure 2M:
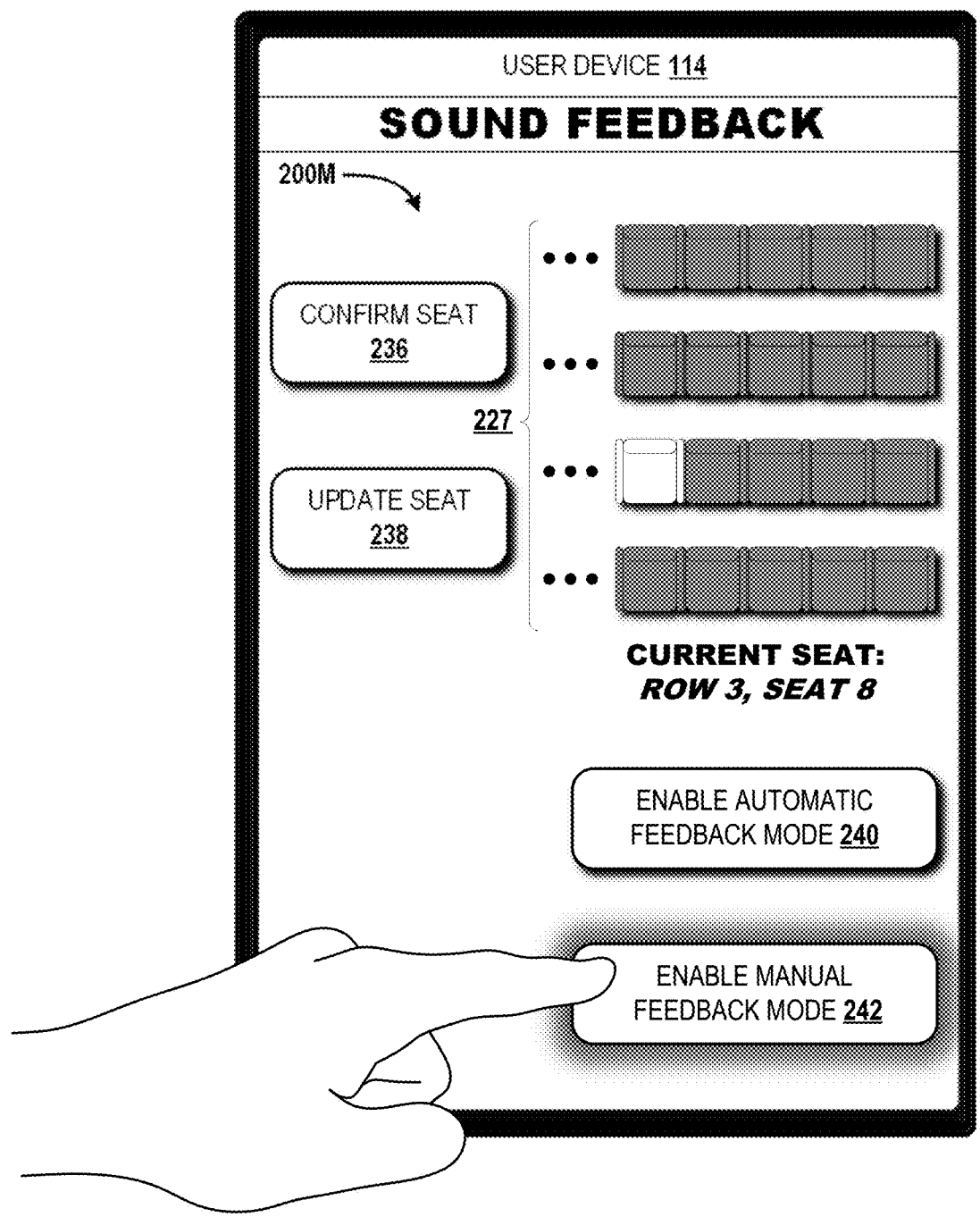
Figure 2N:
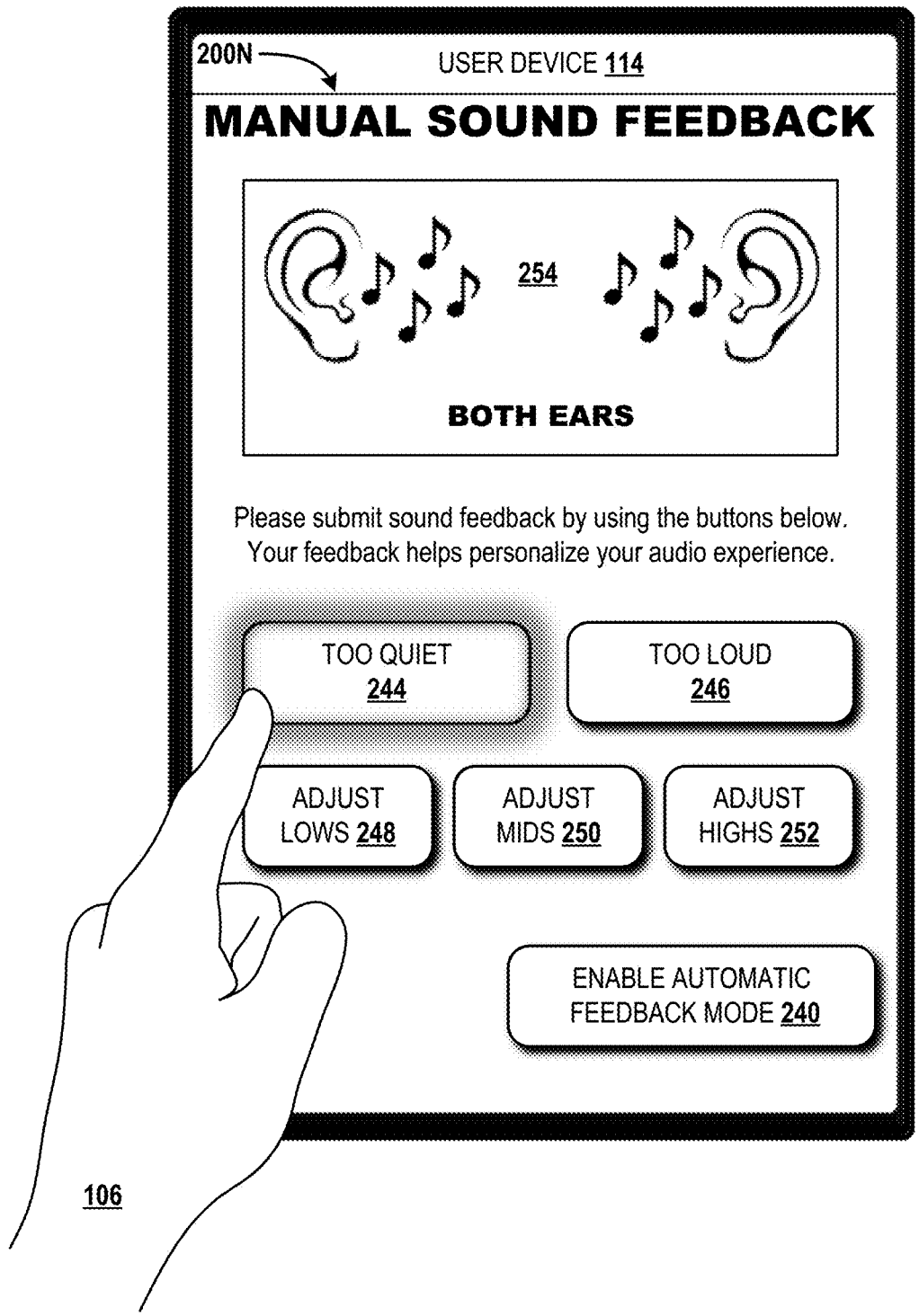

Turning now to FIGS. 2A-2N, graphical user interface ("GUI") diagrams of exemplary user interfaces for implementing aspects of the concepts and technologies disclosed herein will be described, according to illustrative embodiments. The patterns, shapes, fonts, graphics, images, and other design elements of the GUI diagrams are merely intended as examples to aid in explanation of some features disclosed herein. Accordingly, the design of the GUI diagrams should not be construed as being limiting in any way.

Turning first to FIG. 2A, a home screen GUI 200A that can be displayed by a device such as the user device 114 will be described, according to an illustrative embodiment. The illustrated example assumes the user device 114 has a display with a touchscreen for input, as is commonplace today. Those skilled in the art will appreciate the numerous configurations of the user device 114 that can incorporate input via touch and/or different input mechanisms, including keyboard, mouse, controller, voice, touchpad, combinations thereof, and the like. The home screen GUI 200A includes icons representative of the hearing test application 116, the seat assignment application 118, and the sound feedback application 120. Although these applications are shown as independent applications, the functionality thereof can be combined in any way. Moreover, an operating system or firmware of the user device 114 might provide some or all of the functionality of these applications. For purposes of explanation, the hearing test application 116, the seat assignment application 118, and the sound feedback application 120 will be described as independent applications, starting with the hearing test application 116, shown in the illustrated example as being selected, via touch input, received from the user 106. Upon selection of the hearing test application 116 from the home screen GUI 200A, the user device 114 opens the hearing test application 116. It should be understood that the hearing test application 116 can be opened at other times and/or in response to other input. As such, this example is illustrative and should not be construed as being limiting in any way.

Turning now to FIG. 2B, a hearing profile GUI 200B that can be displayed by a device such as the user device 114 will be described, according to an illustrative embodiment. The illustrated hearing profile GUI 200B is presented to the user 106 when a hearing profile option 202 in the hearing test application 116 is selected. The hearing profile GUI 200B shows information such as, in the illustrated example, a user name 204 that uniquely identifies the user 106 (the user name 204 might also be used as a login credential to the hearing test application 116), a last test date 206 to indicate when the last hearing test was performed by/for the user 106, and hearing profiles 208A, 208B (referred to herein collectively as hearing profiles 208 or individually as hearing profile 208) for the left and right ears of the user 106, respectively. The hearing profiles 208 can include any information associated with the results of a hearing test conducted by the hearing test application 116. Alternatively, the hearing profiles 208 can be imported from an outside source, such as a hearing test conducted by or for an audiologist. The level of detail available from the hearing profile 208 can be adjusted based upon the user 106. For example, a percentage of hearing loss for both their left and right ears might be suitable for some of the users 106, while a frequency breakdown that emphasizes which frequency or frequencies he or she has difficulty hearing might be suitable for other users 106. The hearing profiles 208 can be represented visually in text, numbers, characters, emoji, figures, graphs, tables, pictures, images, illustrations, animations, and/or other visual representations, in addition to or as an alternative to audible presentation via the device speaker 124 of the user device 114. The hearing test application 116 also can provide an export option 210 to export hearing test results and/or the hearing profiles 208. Export functionality can include local printing, remote printing, facsimile, email, text message, chat, or any type of data transfer to another entity, such as, for example, the seat assignment system 128, the sound feedback system 130, the venue audio system 108, another user device 114, other device(s), other system(s), other service(s), other user(s) 106, an audiologist or other medical professional, and/or the like.

Turning now to FIG. 2C, an ambient noise test GUI 200C that can be displayed by a device such as the user device 114 will be described, according to an illustrative embodiment. The illustrated ambient noise test GUI 200C can be presented to the user 106 upon selection of a new hearing test option 212 in the hearing test application 116 and/or at other times. The ambient noise test GUI 200C shows an ambient noise meter 214 that measures ambient noise detected by the microphone 122 of the user device 114. When the user 106 is satisfied with the ambient noise conditions, the user 106 can select a continue option 216 to proceed to the hearing test.

Turning now to FIG. 2D, a left ear hearing test GUI 200D that can be displayed by a device such as the user device 114 will be described, according to an illustrative embodiment. The illustrated left ear hearing test GUI 200D is presented to the user 106 upon selection of a left ear test option 218A in the hearing test application 116. The illustrated example uses a tone-based test, although other tests are contemplated, such as the example tests described above. The tone-based test plays different tones and instructs the user 106 to press a hold button 220 until he or she is no longer able to hear the tone in his or her left ear. When the user 106 releases the hold button 220, the hearing test application 116 marks the tone as unheard and updates the hearing profile 208A (i.e., left ear hearing profile). In some contemplated embodiments, the hold button 220 can be replaced and/or supplemented with other controls such as, for example, a press button that the user 106 presses when he or she is no longer able to hear the tone in his or her left ear; two or more buttons (e.g., the hold button 220 and a press button as mentioned); combinations thereof; or the like. As such, the illustrated embodiment should be understood as being illustrative and should not be construed as being limiting in any way. FIG. 2E illustrates a right ear hearing test GUI 200E that can be displayed by a device such as the user device 114. The right ear hearing test GUI 200E can be presented to the user 106 upon selection of a right ear test option 218B in the hearing test application 116 and/or at other times. In the illustrated embodiment, the tone-based test can be repeated for the right ear of the user 106 in a manner that can be substantially similar to the left ear test illustrated and described with reference to FIG. 2D. It should be understood that this example is illustrative, and therefore should not be construed as being limiting in any way.

Turning now to FIG. 2F, a hearing test complete GUI 200F that can be displayed by a device such as the user device 114 will be described, according to an illustrative embodiment. The illustrated hearing test complete GUI 200F is presented to the user 106 after a hearing test is completed. The hearing test complete GUI 200F shows hearing test results 222A, 222B for the left ear and right ear, respectively. The hearing test complete GUI 200F also shows the user name 204 to be associated with the hearing test results 222A, 222B, and a save test results button 224 to save the hearing test results 222A, 222B to the hearing profiles 208A, 208B of the user 106.

Turning now to FIG. 2G, the user device 114 is again shown presenting the home screen GUI 200A (introduced in FIG. 2A). The home screen GUI 200A includes icons representative of the hearing test application 116, the seat assignment application 118, and the sound feedback application 120. Upon selection of the seat assignment application 118 from the home screen GUI 200A, the user device 114 opens the seat assignment application 118. It should be understood that the seat assignment application 118 can be opened at other times and/or in response to other input. As such, this example is illustrative and should not be construed as being limiting in any way.

Turning now to FIG. 2H, a seat selection GUI 200H that can be displayed by a device such as the user device 114 will be described, according to an illustrative embodiment. The illustrated seat selection GUI 200H shows the user name 204 of the user 106 and an upload hearing profile option 226. The seat selection GUI 200H might allow for manual seat selection from a visual representation 227 of the seating 104 at the venue 102. The visual representation 227 can include multiple UI controls/selectors, each of which can correspond to a respective seat shown in the visual representation 227. In accordance with the concepts and technologies disclosed herein, the user 106 can select the upload hearing profile option 226 to upload one or more of the hearing profiles 208 to acquire a seat recommendation made by the seat assignment system 128 based upon information contained in the hearing profiles 208.

Turning now to FIG. 2I, a hearing profile upload GUI 200I that can be displayed by a device such as the user device 114 will be described, according to an illustrative embodiment. The illustrated hearing profile upload GUI 200I shows the user name 204, a local storage device option 228, and a connect option 230. The local storage device option 228 allows the user 106 to select the hearing profiles 208 from a local storage device associated with the user device 114. The connect option 230 allows the user 106 to connect or synchronize the seat assignment application 118 with the hearing test application 116 so that the hearing profiles 208 can be shared. In some embodiments, the hearing test application 116 exposes an application programming interface ("API") that allows other applications, such as the seat assignment application 118, to access the hearing profiles 208. The hearing profiles 208 can be downloaded from a backend of the hearing test application 116 via the network 126, for example.

Turning now to FIG. 2J, a customized seat selection GUI 200J that can be displayed by a device such as the user device 114 will be described, according to an illustrative embodiment. The customized seat selection GUI 200J shows a visual representation of the seating 104 customized based upon the hearing profiles 208. The illustrated customized seat selection GUI 200J shows the user name 204, an auto-select option 232 and a confirm option 234. The user 106 can manually select an available seat and press the confirm option 234 to confirm the seat selection. Alternatively, the user 106 can press the auto-select option 232 that automatically selects an available seat for the user 106 based, at least in part, on the hearing profiles 208. Example processes that can be used to select the seat using the hearing profiles 208 will be illustrated and described in more detail below with reference at least to FIGS. 3 and 4. The user 106 can confirm this auto-selection by pressing the confirm option 234. In the illustrated example, the user 106 has manually selected a seat located at "ROW 3, SEAT 1." The user 106 can press the confirm option 234 to confirm this seat selection.

Turning now to FIG. 2K, the customized seat selection GUI 200J is shown again. In this illustrated example, the user 106 has pressed the auto-select option 232 and the seat assignment application 118 has returned a customized seat selection of a seat located at "ROW 3, SEAT 8." The user 106 can press the confirm option 234 to confirm this seat selection.

Turning now to FIG. 2L, the user device 114 is again shown presenting the home screen GUI 200A (introduced in FIG. 2A). The home screen GUI 200A includes icons representative of the hearing test application 116, the seat assignment application 118, and the sound feedback application 120. Upon selection of the sound feedback application 120 from the home screen GUI 200A, the user device 114 opens the sound feedback application 120. It should be understood that the sound feedback application 120 can be opened at other times and/or in response to other input. As such, this example is illustrative and should not be construed as being limiting in any way.

Turning now to FIG. 2M, a sound feedback GUI 200M that can be displayed by a device such as the user device 114 will be described, according to an illustrative embodiment. The illustrated sound feedback GUI 200M shows the visual representation 227 of a portion of the seating 104 with a seat located at "ROW 3, SEAT 8" selected. This is the same seat selection illustrated in FIG. 2K based upon the user 106 selecting the auto-select option 232. The illustrated sound feedback GUI 200M also shows a confirm seat option 236 and an update seat option 238. The confirm seat option 236 allows the user 106 to confirm his or her seat. The update seat option 238 allows the user 106 to update his or her seat if the seat was changed for any reason. Any sound feedback collected by the sound feedback application 120 can be stored in association with the seat confirmed by the user 106 locally on the user device 114 and/or on the sound feedback system 130.

The illustrated sound feedback GUI 200M also includes an enable automatic feedback mode option 240 and an enable manual feedback mode option 242. When the enable automatic feedback mode option 240 is selected, the microphone 122 of the user device 114 can be initialized to capture the audio output 110. The automatic feedback might be based upon known characteristics of the microphone 122 (e.g., one microphone might be better at picking up low frequencies while another might excel at high frequencies), and might take into account the location of the microphone 122, such as in a pocket of a piece of clothing worn by the user 106. By using the automatic feedback mode option 240 of the sound feedback application 120, the user 106 can focus on their experience listening to the audio output 110 in the venue 102 instead of manually providing their feedback. In some instances, the user 106 might want to provide his or her feedback manually in addition to or as an alternative to the automatic feedback mode. In these instances, the user 106 can select the enable manual feedback mode option 242 in the sound feedback application 120. Of course, manual feedback can be obtained at other times and/or in response to other input and/or requests, so this example is illustrative and should not be construed as being limiting in any way.

Turning now to FIG. 2N, a manual sound feedback GUI 200N that can be displayed by a device such as the user device 114 will be described, according to an illustrative embodiment. The illustrated manual sound feedback GUI 200N shows an ear selection option 254 with both ears selected, although left and right ears can be selected individually for ear-specific sound feedback. The illustrated manual sound feedback GUI 200N also shows a too quiet option 244, a too loud option 246, an adjust low-range frequencies ("adjust lows") option 248, an adjust mid-range frequencies ("adjust mids") option 250, and an adjust high-range frequencies ("adjust highs") option 252. The too quiet option 244 and the too loud option 246 allow the user 106 to provide basic feedback with regard to the volume of the audio output 110. The other options 248, 250, 252 allow the user 106 to adjust sound frequencies similar to an equalizer. In embodiments where the audio output 110 is emitted using audio beamforming, the venue audio system 108 can make adjustments to the volume and/or the equalizer settings based upon the sound feedback provided by the user 106 via the manual sound feedback GUI 200N to personalize the audio experienced by the user 106. The venue audio system 108 can make adjustments based upon the sound feedback. The adjustments can affect the entirety of the audio output 110 or the audio output 110 emitted by a particular speaker or groups of speakers of the speakers 112.

Figure 3:
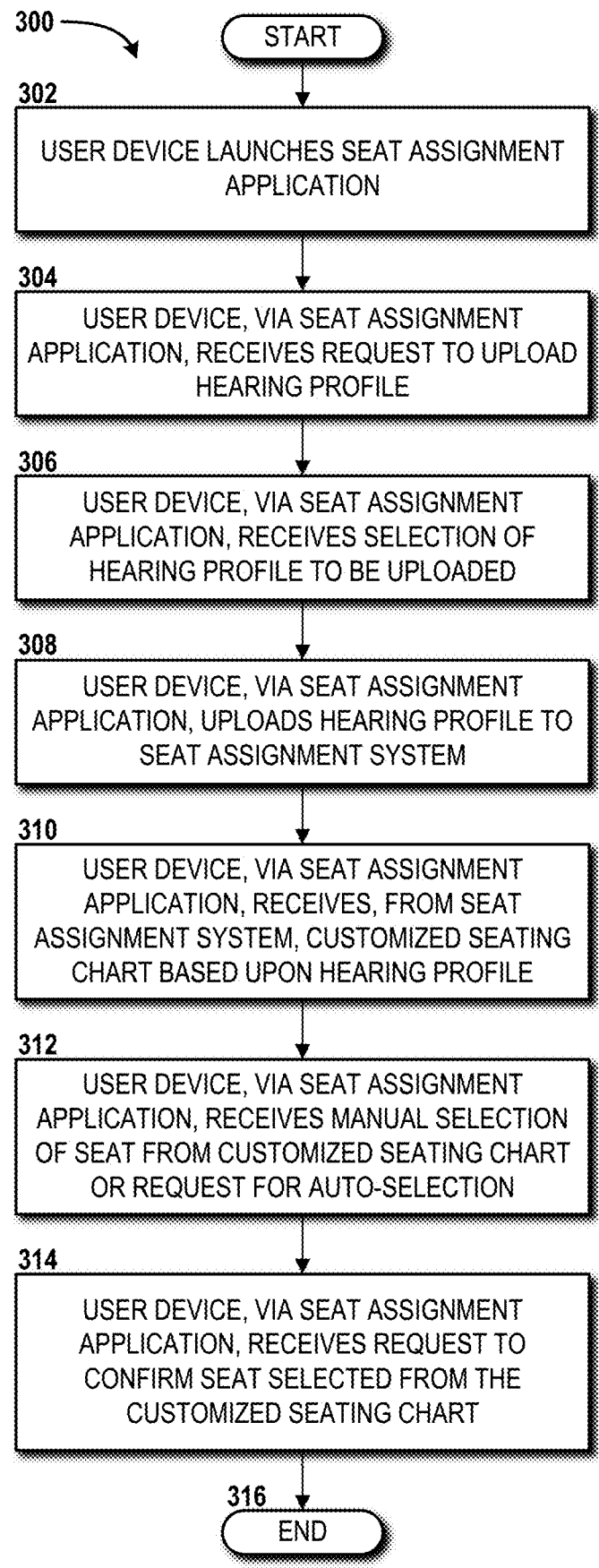
FIG. 3 is a flow diagram illustrating aspects of a method for assigning seats in a venue based, at least in part, upon a hearing profile of a user from the perspective of a user device, according to an illustrative embodiment.

Turning now to FIG. 3, a flow diagram illustrating aspects of a method 300 for assigning seats in the venue 102 based, at least in part, upon the hearing profile 208 of the user 106 will be described from the perspective of the user device 114, according to an illustrative embodiment. It should be understood that the operations of the methods disclosed herein are not necessarily presented in any particular order and that performance of some or all of the operations in an alternative order(s) is possible and is contemplated. The operations have been presented in the demonstrated order for ease of description and illustration. Operations may be added, omitted, and/or performed simultaneously, without departing from the scope of the concepts and technologies disclosed herein.

It also should be understood that the methods disclosed herein can be ended at any time and need not be performed in its entirety. Some or all operations of the methods, and/or substantially equivalent operations, can be performed by execution of computer-readable instructions included on a computer storage media, as defined herein. The term "computer-readable instructions," and variants thereof, as used herein, is used expansively to include routines, applications, application modules, program modules, programs, components, data structures, algorithms, and the like. Computer-readable instructions can be implemented on various system configurations including single-processor or multiprocessor systems or devices, minicomputers, mainframe computers, personal computers, hand-held computing devices, microprocessor-based, programmable consumer electronics, combinations thereof, and the like.

Thus, it should be appreciated that the logical operations described herein are implemented (1) as a sequence of computer implemented acts or program modules running on a computing system and/or (2) as interconnected machine logic circuits or circuit modules within the computing system. The implementation is a matter of choice dependent on the performance and other requirements of the computing system. Accordingly, the logical operations described herein are referred to variously as states, operations, structural devices, acts, or modules. These states, operations, structural devices, acts, and modules may be implemented in software, in firmware, in special purpose digital logic, and any combination thereof. As used herein, the phrase "cause a processor to perform operations" and variants thereof is used to refer to causing one or more processors of the user device 114, the seat assignment system 128, the sound feedback system 130, the venue audio system 108, and/or one or more other computing systems and/or devices disclosed herein to perform operations.

For purposes of illustrating and describing some of the concepts of the present disclosure, the methods disclosed herein are described as being performed, at least in part, by the user device 114, the seat assignment system 128, the sound feedback system 130, and/or the venue audio system 108, as labeled, via execution, by one or more processing components, of one or more software modules. It should be understood that additional and/or alternative devices can provide the functionality described herein via execution of one or more modules, applications, and/or other software. Thus, the illustrated embodiments are illustrative, and should not be viewed as being limiting in any way.

The method 300 will be described with additional reference to FIG. 1 and FIGS. 2G-2K. The method 300 begins and proceeds to operation 302, where the user device 114 launches the seat assignment application 118. From operation 302, the method 300 proceeds to operation 304, where the user device 114, via the seat assignment application 118, receives a request to upload the hearing profile 208 associated with the user 106. The request to upload the hearing profile 208 can be provided to the user device 114 by additional and/or alternative devices or entities, in some embodiments, so this example should be understood as being illustrative and should not be construed as being limiting in any way. The embodiment illustrated in FIGS. 2H-2I shows a request in the form of the user 106 selecting the upload hearing profile option 226 and identifying from where the hearing profile 208 should be uploaded. In some embodiments, the hearing profile 208 is stored locally, such as in memory of the user device 114. Alternatively or additionally, the hearing profile 208 is stored in association with an account the user 106 has in association with the hearing test application 116. As such, the user 106 can request to upload the hearing profile 208 by connecting to the hearing test application 116 (or a backend accessible via the network 126, for example). From operation 304, the method 300 proceeds to operation 306, where the user device 114, via the seat assignment application 118, receives selection of the hearing profile 208 to be uploaded. From operation 306, the method 300 proceeds to operation 308, where the user device 114, via the seat assignment application 118, uploads the hearing profile 208 to the seat assignment system 128.

From operation 308, the method 300 proceeds to operation 310, where the user device 114, via the seat assignment application 118, receives, from the seat assignment system 128, a customized seating chart that includes a visual representation (e.g., the example visual representation 227 shown in FIGS. 2H, 2J, 2K, 2M) of at least a portion of the seating 104 in the venue 102 based, at least in part, upon the hearing profile 208. From operation 310, the method 300 proceeds to operation 312, where the user device 114, via the seat assignment application 118, receives manual selection of a seat from the customized seating chart or a request for auto-selection (e.g., via the auto-select option 232), examples of which are shown in FIGS. 2J and 2K. From operation 312, the method 300 proceeds to operation 314, where the user device 114, via the seat assignment application 118, receives a request to confirm the seat selected (either manually or automatically) from the customized seating chart. The user device 114 can share the confirmed seat assignment with the seat assignment system 128. From operation 314, the method 300 proceeds to operation 316, where the method 300 ends.

Figure 4:
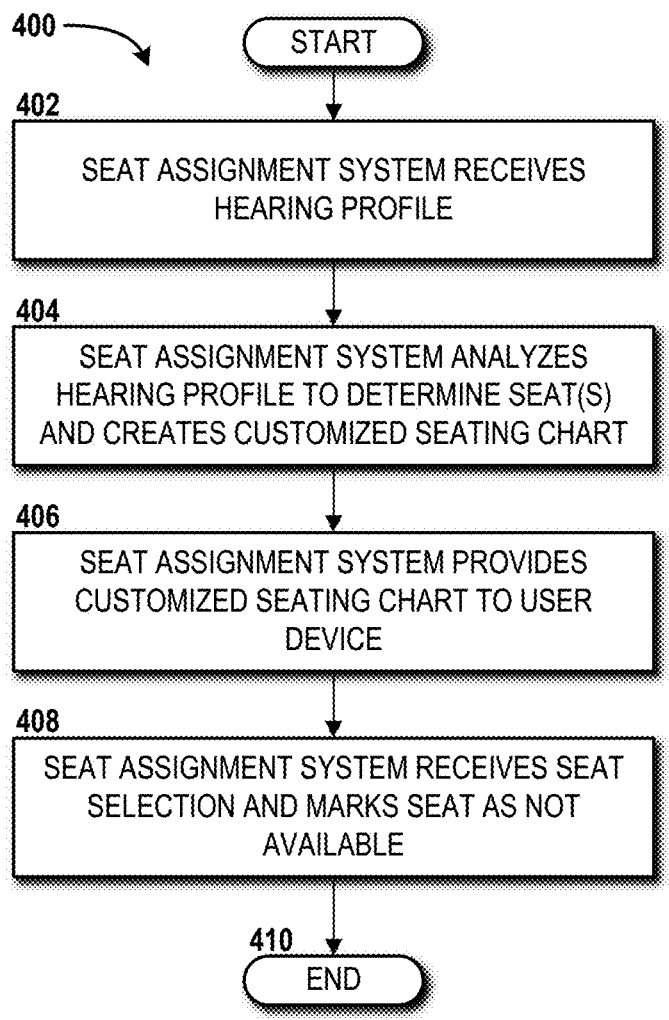
FIG. 4 is a flow diagram illustrating aspects of a method for assigning seats in a venue based, at least in part, upon a hearing profile of a user from the perspective of a seat assignment system, according to an illustrative embodiment.

Turning now to FIG. 4, a flow diagram illustrating aspects of a method 400 for assigning seats in the venue 102 based, at least in part, upon the hearing profile 208 of the user 106 will be described from the perspective of the seat assignment system 128, according to an illustrative embodiment. The method 400 begins and proceeds to operation 402, where the seat assignment system 128 receives the hearing profile 208. In some embodiments, the seat assignment system 128 can receive the hearing profile 208 from the user device 114. In other embodiments, the seat assignment system 128 can receive the hearing profile 208 from an account associated with the user 106. The account might be, for example, an account associated with the hearing test application 116 (or backend thereof).

From operation 402, the method 400 proceeds to operation 404, where the seat assignment system 128 analyzes the hearing profile 208 to determine the seat(s) suitable for the hearing profile 208. The seat assignment system 128 might analyze other information, such as, for example, historical data in the form of sound feedback, other hearing profiles 208 (e.g., of other users attending the venue or an event, etc.), and/or other data collected over time from the user devices 114, the venue audio system 108, and/or other devices/systems in this analysis. The seat assignment system 128 creates the customized seating chart based upon the seat(s) determined to be suitable for the hearing profile 208. From operation 404, the method 400 proceeds to operation 406, where the seat assignment system 128 provides the customized seating chart to the user device 114. From operation 406, the method 400 proceeds to operation 408, where the seat assignment system 128 receives a seat selection from the user device 114 and marks the seat selected as not available so that future seat assignments are not duplicative. From operation 408, the method 400 proceeds to operation 410, where the method 400 ends.

Figure 5:
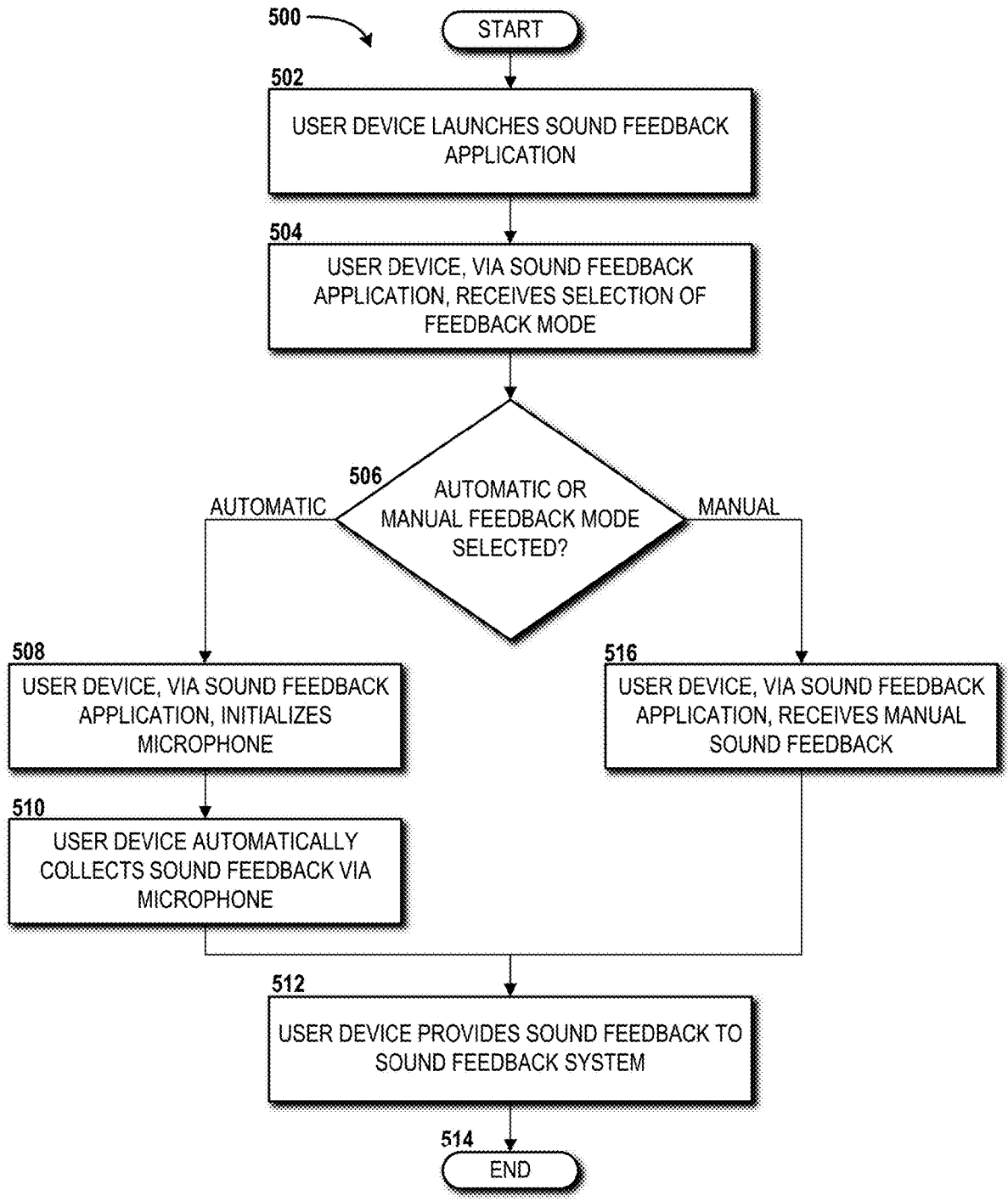
FIG. 5 is a flow diagram illustrating aspects of a method for providing sound feedback from the perspective of a user device, according to an illustrative embodiment.

Turning now to FIG. 5, a flow diagram illustrating aspects of a method 500 for providing sound feedback will be described from the perspective of the user device 114, according to an illustrative embodiment. The method 500 begins and proceeds to operation 502, where the user device 114 launches the sound feedback application 120. From operation 502, the method 500 proceeds to operation 504, where the user device 114, via the sound feedback application 120, receives a selection of a feedback mode (e.g., the enable automatic feedback mode option 240 and the enable manual feedback mode option 242 such as is shown in FIG. 2M). From operation 504, the method 500 proceeds to operation 506, where the user device 114, via the sound feedback application 120, determines whether automatic or manual feedback mode was selected.

In response determining that the automatic feedback mode has been selected, the method 500 proceeds from operation 506 to operation 508, where the user device 114, via the sound feedback application 120, initializes the microphone 122. From operation 508, the method 500 proceeds to operation 510, where the user device 114 automatically collects sound feedback via the microphone 122. From operation 510, the method 500 proceeds to operation 512, where the user device 114 provides the sound feedback to the sound feedback system 130. From operation 512, the method 500 proceeds to operation 514, where the method 500 ends.

Returning to operation 506, in response to detecting that the manual feedback mode has been selected, the method 500 proceeds from operation 506 to operation 516, where the user device 114, via the sound feedback application 120, receives manual sound feedback. In some embodiments, the user device 114 can receive manual sound feedback from the user 106 via the manual sound feedback GUI 200N illustrated and described with reference to FIG. 2N. Other methods of providing manual sound feedback are contemplated, including natural language and specific voice commands. From operation 516, the method 500 proceeds to operation 514, where the method 500 ends.

Figure 6:
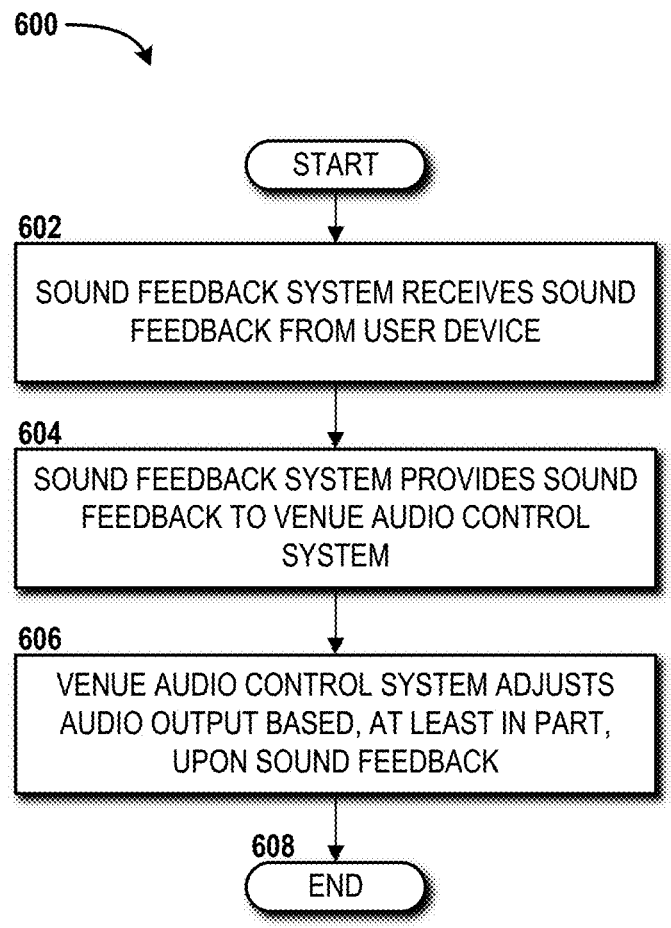
FIG. 6 is a flow diagram illustrating aspects of a method for providing sound feedback from the perspective of a sound feedback system, according to an illustrative embodiment.

Turning now to FIG. 6, a flow diagram illustrating aspects of a method 600 for providing sound feedback will be described from the perspective of the sound feedback system 130, according to an illustrative embodiment. The method 600 begins and proceeds to operation 602, where the sound feedback system 130 receives sound feedback from the user device 114. The sound feedback can be collected by the user device 114 automatically or manually as described above. From operation 602, the method 600 proceeds to operation 604, where the sound feedback system 130 provides the sound feedback to the venue audio system 108. From operation 604, the method 600 proceeds to operation 606, where the venue audio system 108 adjust the audio output 110 based, at least in part, upon the sound feedback received from the sound feedback system 130. From operation 606, the method 600 proceeds to operation 608, where the method 600 ends.

Figure 7:
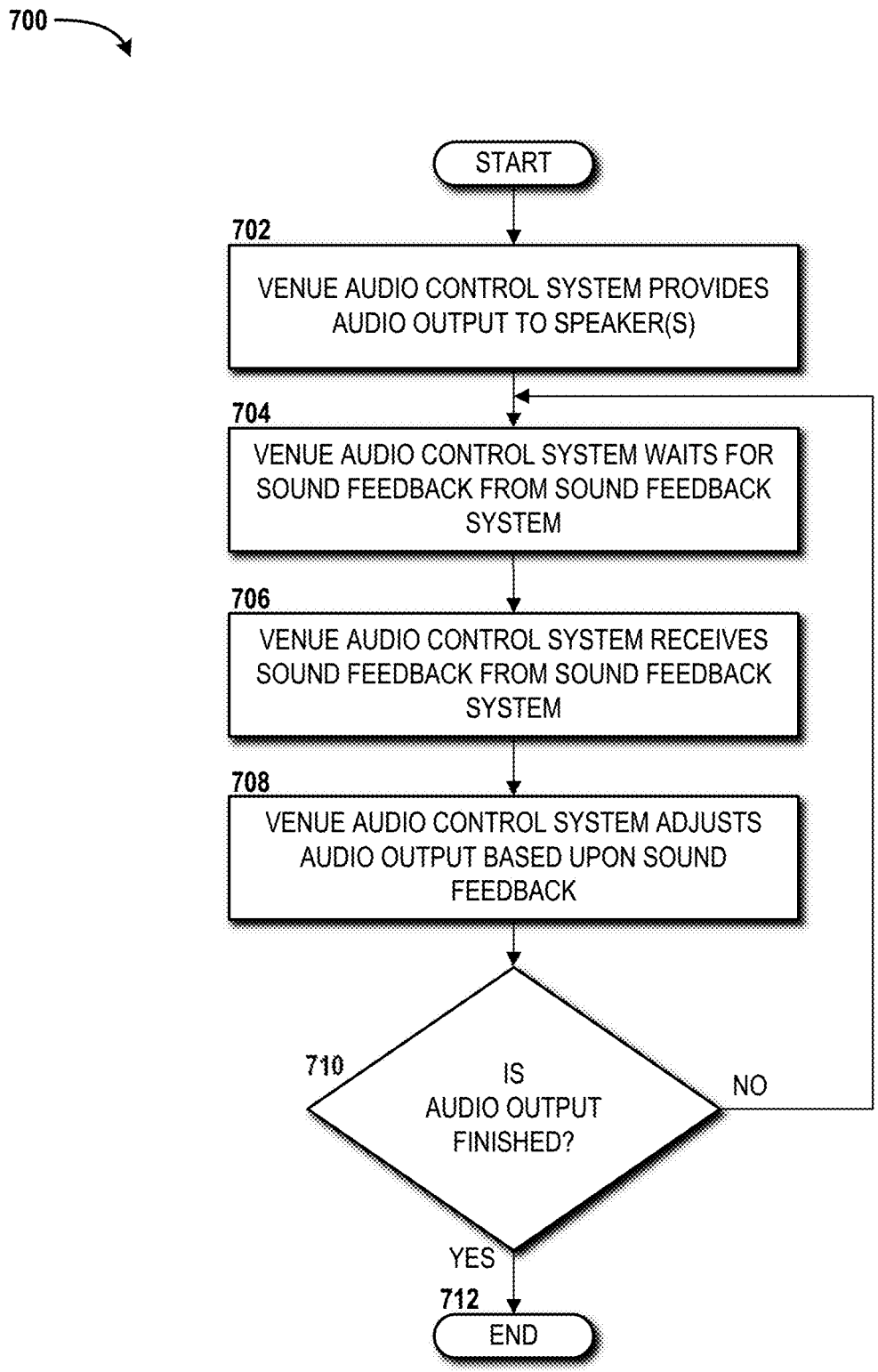
FIG. 7 is a flow diagram illustrating aspects of a method for controlling an audio output in a venue from the perspective of a venue audio system, according to an illustrative embodiment.

Turning now to FIG. 7, a flow diagram illustrating aspects of a method 700 for controlling the audio output 110 in the venue 102 will be described from the perspective of the venue audio system 108, according to an illustrative embodiment. The method 700 begins and proceeds to operation 702, where the venue audio system 108 provides the audio output 110 to at least one of the speakers 112 that, in turn, emit the audio output 110 to be heard by the users 106 present in the venue 102.

From operation 702, the method 700 proceeds to operation 704, where the venue audio system 108 waits for sound feedback from the sound feedback system 130. Alternatively or additionally, the venue audio system 108 can wait for sound feedback from other sources, such as directly from the user device 114 executing the sound feedback application 120. From operation 704, the method 700 proceeds to operation 706, where the venue audio system 108 receives the sound feedback from the sound feedback system 130 and/or other sources. From operation 706, the method 700 proceeds to operation 708, where the venue audio system 108 adjusts the audio output 110 based upon the sound feedback.

From operation 708, the method 700 proceeds to operation 710, where the venue audio system 108 determines if the audio output 110 is finished. If the venue audio system 108 determines that the audio output 110 is not finished, the method 700 returns to operation 704, where the venue audio system 108 again waits for sound feedback from the sound feedback system 130. Alternatively or additionally, the venue audio system 108 can wait for sound feedback from other sources, such as directly from the user device 114 executing the sound feedback application 120. The remaining operations of the method 700 proceed as described above until, at operation 710, the venue audio system 108 determines that the audio output 110 is finished, after which the method 700 proceeds to operation 712, where the method 700 ends.

Figure 8:
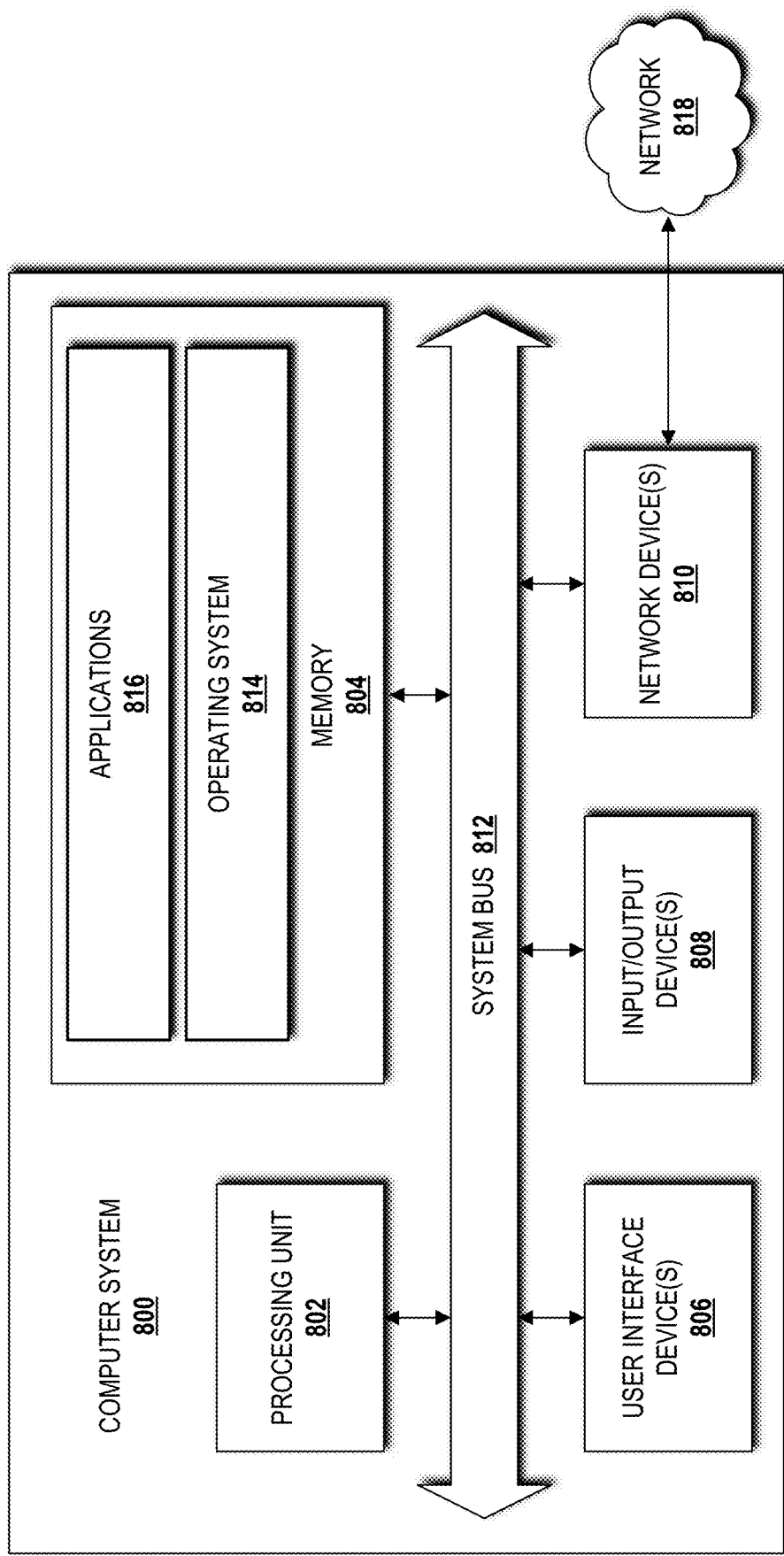
FIG. 8 is a block diagram illustrating an example computer system capable of implementing aspects of the embodiments presented herein.

FIG. 8 is a block diagram illustrating a computer system 800 configured to perform various operations disclosed herein. The computer system 800 includes a processing unit 802, a memory 804, one or more user interface devices 806, one or more input/output ("I/O") devices 808, and one or more network devices 810, each of which is operatively connected to a system bus 812. The system bus 812 enables bi-directional communication between the processing unit 802, the memory 804, the user interface devices 806, the I/O devices 808, and the network devices 810. In some embodiments, the venue audio system 108, the user device 114, the seat assignment system 128, the sound feedback system 130, servers and/or other systems associated with the hearing test application 116, the seat assignment application 118, and/or the sound feedback application 120, one or more components thereof, some combination thereof is/are configured, at least in part, like the computer system 800. It should be understood, however, that the venue audio system 108, the user device 114, the seat assignment system 128, the sound feedback system 130, servers and/or other systems associated with the hearing test application 116, the seat assignment application 118, and/or the sound feedback application 120 might include additional functionality or include less functionality than now described.

The processing unit 802 might be a standard central processor that performs arithmetic and logical operations, a more specific purpose programmable logic controller ("PLC"), a programmable gate array, or other type of processor known to those skilled in the art and suitable for controlling the operation of the computer system 800. Processing units are generally known, and therefore are not described in further detail herein.

The memory 804 communicates with the processing unit 802 via the system bus 812. In some embodiments, the memory 804 is operatively connected to a memory controller (not shown) that enables communication with the processing unit 802 via the system bus 812. The illustrated memory 804 includes an operating system 814 and one or more applications 816.

The operating system 814 can include, but is not limited to, members of the WINDOWS, WINDOWS CE, WINDOWS MOBILE, and/or WINDOWS PHONE families of operating systems from MICROSOFT CORPORATION, the LINUX family of operating systems, the SYMBIAN family of operating systems from SYMBIAN LIMITED, the BREW family of operating systems from QUALCOMM CORPORATION, the MAC OS and/or iOS families of operating systems from APPLE INC., the FREEBSD family of operating systems, the SOLARIS family of operating systems from ORACLE CORPORATION, other operating systems such as proprietary operating systems, and the like.

The user interface devices 806 may include one or more devices with which a user accesses the computer system 800. The user interface devices 806 may include, but are not limited to, computers, servers, personal digital assistants, telephones (e.g., cellular, IP, or landline), or any suitable computing devices. The I/O devices 808 enable a user to interface with the program modules. In one embodiment, the I/O devices 808 are operatively connected to an I/O controller (not shown) that enables communication with the processing unit 802 via the system bus 812. The I/O devices 808 may include one or more input devices, such as, but not limited to, a keyboard, a mouse, a touchscreen, or an electronic stylus. Further, the I/O devices 808 may include one or more output devices, such as, but not limited to, a display screen or a printer.

The network devices 810 enable the computer system 800 to communicate with other networks or remote systems via a network 818. Examples of the network devices 810 include, but are not limited to, a modem, a radio frequency ("RF") or infrared ("IR") transceiver, a telephonic interface, a bridge, a router, or a network card. The network 818 may include a wireless network such as, but not limited to, a WLAN such as a WI-FI network, a WWAN, a wireless PAN ("WPAN") such as BLUETOOTH, or a wireless MAN ("WMAN"). Alternatively, the network 818 may be a wired network such as, but not limited to, a WAN such as the Internet, a LAN such as the Ethernet, a wired PAN, or a wired MAN.

Figure 9:
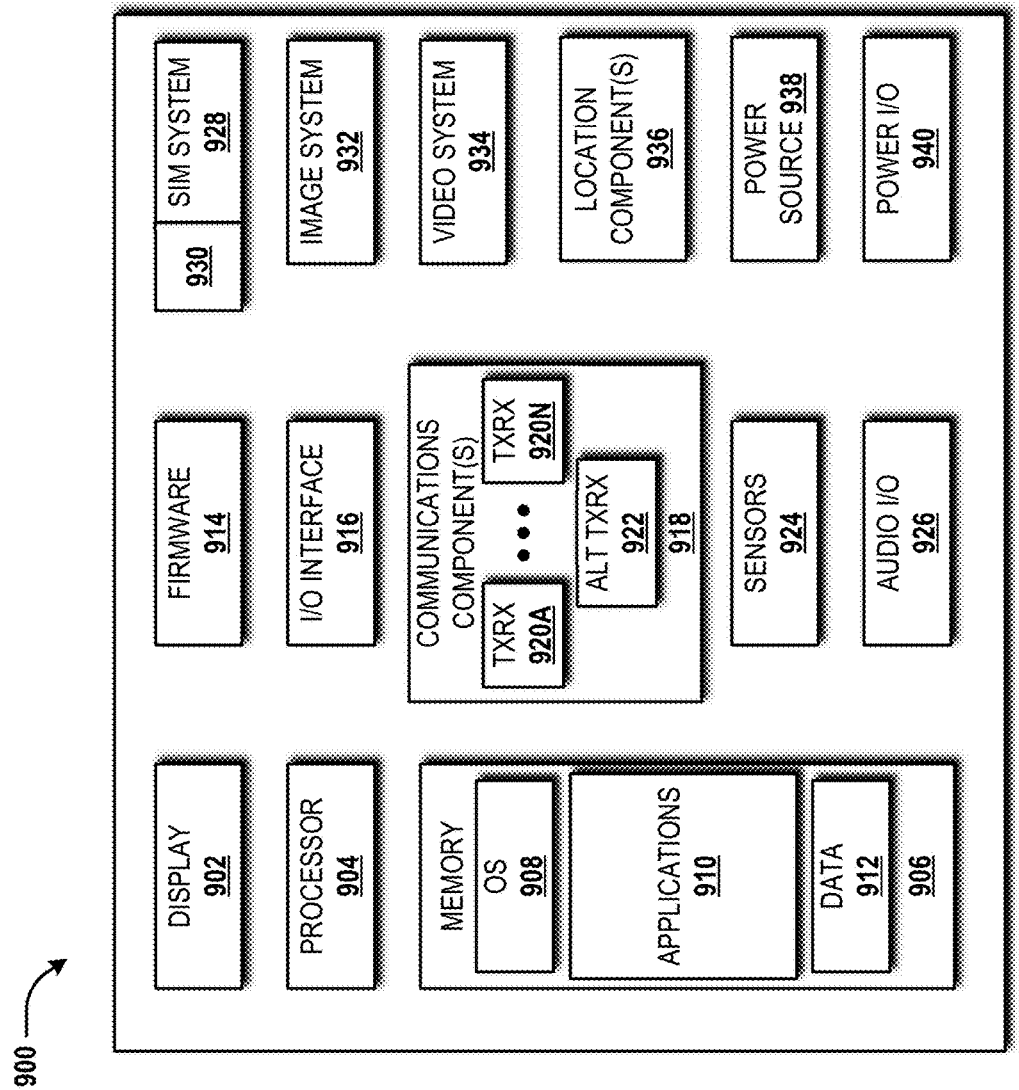
FIG. 9 is a block diagram illustrating an example mobile device capable of implementing aspects of the embodiments disclosed herein.

Turning now to FIG. 9, an illustrative mobile device 900 and components thereof will be described. In some embodiments, the venue audio system 108, the user device 114, the seat assignment system 128, the sound feedback system 130, servers and/or other systems associated with the hearing test application 116, the seat assignment application 118, and/or the sound feedback application 120, described above with reference to FIG. 1 can be configured as and/or can have an architecture similar or identical to the mobile device 900 described herein in FIG. 9. It should be understood, however, that the venue audio system 108, the user device 114, the seat assignment system 128, the sound feedback system 130, servers and/or other systems associated with the hearing test application 116, the seat assignment application 118, and/or the sound feedback application 120 may or may not include the functionality described herein with reference to FIG. 9. While connections are not shown between the various components illustrated in FIG. 9, it should be understood that some, none, or all of the components illustrated in FIG. 9 can be configured to interact with one another to carry out various device functions. In some embodiments, the components are arranged so as to communicate via one or more busses (not shown). Thus, it should be understood that FIG. 9 and the following description are intended to provide a general understanding of a suitable environment in which various aspects of embodiments can be implemented, and should not be construed as being limiting in any way.

As illustrated in FIG. 9, the mobile device 900 can include a display 902 for displaying data. According to various embodiments, the display 902 can be configured to display network connection information, various GUI elements, text, images, video, virtual keypads and/or keyboards, messaging data, notification messages, metadata, Internet content, device status, time, date, calendar data, device preferences, map and location data, combinations thereof, and/or the like. The mobile device 900 also can include a processor 904 and a memory or other data storage device ("memory") 906. The processor 904 can be configured to process data and/or can execute computer-executable instructions stored in the memory 906. The computer-executable instructions executed by the processor 904 can include, for example, an operating system 908, one or more applications 910, other computer-executable instructions stored in the memory 906, or the like. In some embodiments, the applications 910 also can include a UI application (not illustrated in FIG. 9). In some embodiments, the applications 910 can include the hearing test application 116, the seat assignment application 118, and the sound feedback application 120 (all shown in FIG. 1).

The UI application can interface with the operating system 908 to facilitate user interaction with functionality and/or data stored at the mobile device 900 and/or stored elsewhere. In some embodiments, the operating system 908 can include a member of the SYMBIAN OS family of operating systems from SYMBIAN LIMITED, a member of the WINDOWS MOBILE OS and/or WINDOWS PHONE OS families of operating systems from MICROSOFT CORPORATION, a member of the PALM WEBOS family of operating systems from HEWLETT PACKARD CORPORATION, a member of the BLACKBERRY OS family of operating systems from RESEARCH IN MOTION LIMITED, a member of the IOS family of operating systems from APPLE INC., a member of the ANDROID OS family of operating systems from GOOGLE INC., and/or other operating systems. These operating systems are merely illustrative of some contemplated operating systems that may be used in accordance with various embodiments of the concepts and technologies described herein and therefore should not be construed as being limiting in any way.

The UI application can be executed by the processor 904 to aid a user in data communications, entering/deleting data, entering and setting user IDs and passwords for device access, configuring settings, manipulating content and/or settings, multimode interaction, interacting with other applications 910, and otherwise facilitating user interaction with the operating system 908, the applications 910, and/or other types or instances of data 912 that can be stored at the mobile device 900.

The applications 910, the data 912, and/or portions thereof can be stored in the memory 906 and/or in a firmware 914, and can be executed by the processor 904. The firmware 914 also can store code for execution during device power up and power down operations. It can be appreciated that the firmware 914 can be stored in a volatile or non-volatile data storage device including, but not limited to, the memory 906 and/or a portion thereof.

The mobile device 900 also can include an input/output ("I/O") interface 916. The I/O interface 916 can be configured to support the input/output of data such as location information, presence status information, user IDs, passwords, and application initiation (start-up) requests. In some embodiments, the I/O interface 916 can include a hardwire connection such as a universal serial bus ("USB") port, a mini-USB port, a micro-USB port, an audio jack, a PS2 port, an IEEE 1394 ("FIREWIRE") port, a serial port, a parallel port, an Ethernet (RJ45) port, an RJ11 port, a proprietary port, combinations thereof, or the like. In some embodiments, the mobile device 900 can be configured to synchronize with another device to transfer content to and/or from the mobile device 900. In some embodiments, the mobile device 900 can be configured to receive updates to one or more of the applications 910 via the I/O interface 916, though this is not necessarily the case. In some embodiments, the I/O interface 916 accepts I/O devices such as keyboards, keypads, mice, interface tethers, printers, plotters, external storage, touch/multi-touch screens, touch pads, trackballs, joysticks, microphones, remote control devices, displays, projectors, medical equipment (e.g., stethoscopes, heart monitors, and other health metric monitors), modems, routers, external power sources, docking stations, combinations thereof, and the like. It should be appreciated that the I/O interface 916 may be used for communications between the mobile device 900 and a network device or local device.

The mobile device 900 also can include a communications component 918. The communications component 918 can be configured to interface with the processor 904 to facilitate wired and/or wireless communications with one or more networks. In some embodiments, the communications component 918 includes a multimode communications subsystem for facilitating communications via the cellular network and one or more other networks.

The communications component 918, in some embodiments, includes one or more transceivers. The one or more transceivers, if included, can be configured to communicate over the same and/or different wireless technology standards with respect to one another. For example, in some embodiments, one or more of the transceivers of the communications component 918 may be configured to communicate using GSM, CDMAONE, CDMA2000, LTE, and various other 2G, 2.5G, 3G, 4G, 4.5G, 5G, and greater generation technology standards. Moreover, the communications component 918 may facilitate communications over various channel access methods (which may or may not be used by the aforementioned standards) including, but not limited to, TDMA, FDMA, W-CDMA, OFDM, SDMA, and the like.

In addition, the communications component 918 may facilitate data communications using GPRS, EDGE, the HSPA protocol family including HSDPA, EUL or otherwise termed HSUPA, HSPA+, and various other current and future wireless data access standards. In the illustrated embodiment, the communications component 918 can include a first transceiver ("TxRx") 920A that can operate in a first communications mode (e.g., GSM). The communications component 918 also can include an $N^{th}$ transceiver ("TxRx") 920N that can operate in a second communications mode relative to the first transceiver 920A (e.g., UMTS). While two transceivers 920A-920N (hereinafter collectively and/or generically referred to as "transceivers 920") are shown in FIG. 9, it should be appreciated that less than two, two, and/or more than two transceivers 920 can be included in the communications component 918.

The communications component 918 also can include an alternative transceiver ("Alt TxRx") 922 for supporting other types and/or standards of communications. According to various contemplated embodiments, the alternative transceiver 922 can communicate using various communications technologies such as, for example, WI-FI, WIMAX, BLUETOOTH, infrared, infrared data association ("IRDA"), near field communications ("NFC"), other RF technologies, combinations thereof, and the like. In some embodiments, the communications component 918 also can facilitate reception from terrestrial radio networks, digital satellite radio networks, internet-based radio service networks, combinations thereof, and the like. The communications component 918 can process data from a network such as the Internet, an intranet, a broadband network, a WI-FI hotspot, an Internet service provider ("ISP"), a digital subscriber line ("DSL") provider, a broadband provider, combinations thereof, or the like.

The mobile device 900 also can include one or more sensors 924. The sensors 924 can include temperature sensors, light sensors, air quality sensors, movement sensors, accelerometers, magnetometers, gyroscopes, infrared sensors, orientation sensors, noise sensors, microphones proximity sensors, combinations thereof, and/or the like. Additionally, audio capabilities for the mobile device 900 may be provided by an audio I/O component 926. The audio I/O component 926 of the mobile device 900 can include one or more speakers for the output of audio signals, one or more microphones for the collection and/or input of audio signals, and/or other audio input and/or output devices.

The illustrated mobile device 900 also can include a subscriber identity module ("SIM") system 928. The SIM system 928 can include a universal SIM ("USIM"), a universal integrated circuit card ("UICC") and/or other identity devices. The SIM system 928 can include and/or can be connected to or inserted into an interface such as a slot interface 930. In some embodiments, the slot interface 930 can be configured to accept insertion of other identity cards or modules for accessing various types of networks. Additionally, or alternatively, the slot interface 930 can be configured to accept multiple subscriber identity cards. Because other devices and/or modules for identifying users and/or the mobile device 900 are contemplated, it should be understood that these embodiments are illustrative, and should not be construed as being limiting in any way.

The mobile device 900 also can include an image capture and processing system 932 ("image system"). The image system 932 can be configured to capture or otherwise obtain photos, videos, and/or other visual information. As such, the image system 932 can include cameras, lenses, charge-coupled devices ("CCDs"), combinations thereof, or the like. The mobile device 900 may also include a video system 934. The video system 934 can be configured to capture, process, record, modify, and/or store video content. Photos and videos obtained using the image system 932 and the video system 934, respectively, may be added as message content to an MMS message, email message, and sent to another device. The video and/or photo content also can be shared with other devices via various types of data transfers via wired and/or wireless communication devices as described herein.

The mobile device 900 also can include one or more location components 936. The location components 936 can be configured to send and/or receive signals to determine a geographic location of the mobile device 900. According to various embodiments, the location components 936 can send and/or receive signals from global positioning system ("GPS") devices, assisted-GPS ("A-GPS") devices, WI-FI/WIMAX and/or cellular network triangulation data, combinations thereof, and the like. The location component 936 also can be configured to communicate with the communications component 918 to retrieve triangulation data for determining a location of the mobile device 900. In some embodiments, the location component 936 can interface with cellular network nodes, telephone lines, satellites, location transmitters and/or beacons, wireless network transmitters and receivers, combinations thereof, and the like. In some embodiments, the location component 936 can include and/or can communicate with one or more of the sensors 924 such as a compass, an accelerometer, and/or a gyroscope to determine the orientation of the mobile device 900. Using the location component 936, the mobile device 900 can generate and/or receive data to identify its geographic location, or to transmit data used by other devices to determine the location of the mobile device 900. The location component 936 may include multiple components for determining the location and/or orientation of the mobile device 900.

The illustrated mobile device 900 also can include a power source 938. The power source 938 can include one or more batteries, power supplies, power cells, and/or other power subsystems including alternating current ("AC") and/or direct current ("DC") power devices. The power source 938 also can interface with an external power system or charging equipment via a power I/O component 940. Because the mobile device 900 can include additional and/or alternative components, the above embodiment should be understood as being illustrative of one possible operating environment for various embodiments of the concepts and technologies described herein. The described embodiment of the mobile device 900 is illustrative, and should not be construed as being limiting in any way.

As used herein, communication media includes computer-executable instructions, data structures, program modules, or other data in a modulated data signal such as a carrier wave or other transport mechanism and includes any delivery media. The term "modulated data signal" means a signal that has one or more of its characteristics changed or set in a manner as to encode information in the signal. By way of example, and not limitation, communication media includes wired media such as a wired network or direct-wired connection, and wireless media such as acoustic, RF, infrared, and other wireless media. Combinations of any of the above should also be included within the scope of computer-readable media.

By way of example, and not limitation, computer storage media may include volatile and non-volatile, removable and non-removable media implemented in any method or technology for storage of information such as computer-executable instructions, data structures, program modules, or other data. For example, computer media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the mobile device 900 or other devices or computers described herein, such as the computer system 800 described above with reference to FIG. 8. For purposes of the claims, the phrase "computer-readable storage medium" and variations thereof, does not include waves, signals, and/or other transitory and/or intangible communication media, per se.

Encoding the software modules presented herein also may transform the physical structure of the computer-readable media presented herein. The specific transformation of physical structure may depend on various factors, in different implementations of this description. Examples of such factors may include, but are not limited to, the technology used to implement the computer-readable media, whether the computer-readable media is characterized as primary or secondary storage, and the like. For example, if the computer-readable media is implemented as semiconductor-based memory, the software disclosed herein may be encoded on the computer-readable media by transforming the physical state of the semiconductor memory. For example, the software may transform the state of transistors, capacitors, or other discrete circuit elements constituting the semiconductor memory. The software also may transform the physical state of such components in order to store data thereupon.

As another example, the computer-readable media disclosed herein may be implemented using magnetic or optical technology. In such implementations, the software presented herein may transform the physical state of magnetic or optical media, when the software is encoded therein. These transformations may include altering the magnetic characteristics of particular locations within given magnetic media. These transformations also may include altering the physical features or characteristics of particular locations within given optical media, to change the optical characteristics of those locations. Other transformations of physical media are possible without departing from the scope and spirit of the present description, with the foregoing examples provided only to facilitate this discussion.

In light of the above, it should be appreciated that many types of physical transformations may take place in the mobile device 900 in order to store and execute the software components presented herein. It is also contemplated that the mobile device 900 may not include all of the components shown in FIG. 9, may include other components that are not explicitly shown in FIG. 9, or may utilize an architecture completely different than that shown in FIG. 9.

Turning now to FIG. 10, details of a network 1000 are illustrated, according to an illustrative embodiment. The network 1000 includes a cellular network 1002, a packet data network 1004, and a circuit switched network 1006 (e.g., a public switched telephone network).

The cellular network 1002 includes various components such as, but not limited to, base transceiver stations ("BTSs"), Node-Bs or e-Node-Bs, base station controllers ("BSCs"), radio network controllers ("RNCs"), mobile switching centers ("MSCs"), mobility management entities ("MMEs"), short message service centers ("SMSCs"), multimedia messaging service centers ("MMSCs"), home location registers ("HLRs"), home subscriber servers ("HSSs"), visitor location registers ("VLRs"), charging platforms, billing platforms, voicemail platforms, GPRS core network components, location service nodes, and the like. The cellular network 1002 also includes radios and nodes for receiving and transmitting voice, data, and combinations thereof to and from radio transceivers, networks, the packet data network 1004, and the circuit switched network 1006.

A mobile communications device 1008, such as, for example, a cellular telephone, a user equipment, a mobile terminal, a PDA, a laptop computer, a handheld computer, the user device 114, and combinations thereof, can be operatively connected to the cellular network 1002. The cellular network 1002 can be configured as a 2G Global System for Mobile communications ("GSM") network and can provide data communications via General Packet Radio Service ("GPRS") and/or Enhanced Data services for Global Evolution ("EDGE"). Additionally, or alternatively, the cellular network 1002 can be configured as a 3G Universal Mobile Telecommunications System ("UMTS") network and can provide data communications via the High-Speed Packet Access ("HSPA") protocol family, for example, High-Speed Downlink Packet Access ("HSDPA"), Enhanced Uplink ("EUL") (also referred to as High-Speed Uplink Packet Access ("HSUPA"), and HSPA+. The cellular network 1002 also is compatible with 4G mobile communications standards such as Long-Term Evolution ("LTE"), or the like, as well as evolved and future mobile standards.

The packet data network 1004 includes various devices, for example, servers, computers, databases, and other devices in communication with one another, as is generally known. In some embodiments, the packet data network 1004 is or includes one or more WI-FI networks, each of which can include one or more WI-FI access points, routers, switches, and other WI-FI network components. The packet data network 1004 devices are accessible via one or more network links. The servers often store various files that are provided to a requesting device such as, for example, a computer, a terminal, a smartphone, or the like. Typically, the requesting device includes software (a "browser") for executing a web page in a format readable by the browser or other software. Other files and/or data may be accessible via "links" in the retrieved files, as is generally known. In some embodiments, the packet data network 1004 includes or is in communication with the Internet. The circuit switched network 1006 includes various hardware and software for providing circuit switched communications. The circuit switched network 1006 may include, or may be, what is often referred to as a plain old telephone system ("POTS"). The functionality of a circuit switched network 1006 or other circuit-switched network are generally known and will not be described herein in detail.

The illustrated cellular network 1002 is shown in communication with the packet data network 1004 and a circuit switched network 1006, though it should be appreciated that this is not necessarily the case. One or more Internet-capable devices 1010, for example, the user device 114, the venue audio system 108, the user device 114, the seat assignment system 128, the sound feedback system 130, servers and/or other systems associated with the hearing test application 116, the seat assignment application 118, and/or the sound feedback application 120, a PC, a laptop, a portable device, or another suitable device, can communicate with one or more cellular networks 1002, and devices connected thereto, through the packet data network 1004. It also should be appreciated that the Internet-capable device 1010 can communicate with the packet data network 1004 through the circuit switched network 1006, the cellular network 1002, and/or via other networks (not illustrated).

As illustrated, a communications device 1012, for example, a telephone, facsimile machine, modem, computer, or the like, can be in communication with the circuit switched network 1006, and therethrough to the packet data network 1004 and/or the cellular network 1002. It should be appreciated that the communications device 1012 can be an Internet-capable device, and can be substantially similar to the Internet-capable device 1010.

Based on the foregoing, it should be appreciated that concepts and technologies for venue seat assignment based upon hearing profiles have been disclosed herein. Although the subject matter presented herein has been described in language specific to computer structural features, methodological and transformative acts, specific computing machinery, and computer-readable media, it is to be understood that the invention defined in the appended claims is not necessarily limited to the specific features, acts, or media described herein. Rather, the specific features, acts and mediums are disclosed as example forms of implementing the claims.

The subject matter described above is provided by way of illustration only and should not be construed as limiting. Various modifications and changes may be made to the subject matter described herein without following the example embodiments and applications illustrated and described, and without departing from the true spirit and scope of the subject disclosure.

I claim:

1. A device comprising:
a display;
a microphone;
a processor; and
a memory having computer-executable instructions stored thereon that, when executed by the processor, cause the processor to perform operations comprising
receiving a request to upload a hearing profile of a user,
uploading the hearing profile of the user to a seat assignment system associated with a venue,
receiving, from the seat assignment system, a customized seating chart comprising a visual representation of at least a portion of seating in the venue determined based, at least in part, upon the hearing profile of the user and sound feedback associated with at least the portion of seating in the venue provided by users while listening to audio outputs at the venue,
presenting, on the display, a graphical user interface that shows the customized seating chart,
selecting, from the customized seating chart, a seat for the user from at least the portion of the seating in the venue,
capturing, by the microphone, audio output at the seat selected for the user,
determining sound feedback associated with the audio output captured by the microphone, wherein the sound feedback associated with the audio output captured by the microphone is representative of sound characteristics of the audio output and takes into account at least one of a characteristic of the microphone that captured the audio output or a location of the microphone in association with the user, and
providing the sound feedback associated with the audio output captured by the microphone to a venue audio system, wherein the venue audio system adjusts the audio output based on the sound feedback associated with the audio output captured by the microphone to personalize the audio output for the user.

2. The device of claim 1, wherein the operations further comprise presenting, on the display, a graphical user interface that shows an upload hearing profile option, and wherein receiving the request to upload the hearing profile of the user comprises the upload hearing profile option being selected.

3. The device of claim 1, wherein the operations further comprise generating the hearing profile of the user based on at least one of hearing test results from a hearing test performed by a hearing test application of the device or hearing test results imported by the hearing test application from equipment external to the device.

4. The device of claim 1, wherein selecting, from the customized seating chart, the seat for the user from at least the portion of the seating in the venue comprises:
receiving selection of an automatic seat selection option provided by the graphical user interface that shows the customized seating chart; and
automatically selecting an available seat from at least the portion of the seating in the customized seating chart as the seat for the user.

5. The device of claim 1, wherein selecting, from the customized seating chart, the seat for the user from at least the portion of the seating in the venue comprises receiving manual selection, via a user input, of an available seat from at least the portion of the seating in the customized seating chart as the seat for the user.

6. The device of claim 1, wherein the operations further comprise:
presenting, on the display, a manual sound feedback graphical user interface including at least one option associated with a first level of manual sound feedback and at least one option associated with a second level of manual sound feedback, wherein the first level of manual sound feedback and the second level of manual sound feedback are based on knowledge of the user; and
receiving, via the manual sound feedback graphical user interface, at least one of the first level of manual sound feedback or the second level of manual sound feedback.

7. The device of claim 6, wherein providing the sound feedback associated with the audio output captured by the microphone to the venue audio system comprises providing the sound feedback associated with the audio output captured by the microphone and the at least one of the first level of manual sound feedback or the second level of manual sound feedback to the venue audio system, and wherein the venue audio system adjusts the audio output based on the sound feedback associated with the audio output captured by the microphone to personalize the audio output for the user comprises the venue audio system adjusting the audio output based on the sound feedback associated with the audio output captured by the microphone and the at least one of the first level of manual sound feedback or the second level of manual sound feedback to personalize the audio output for the user.

8. A computer-readable storage medium having computer-executable instructions stored thereon that, when executed by a processor of a device comprising a display and a microphone, cause the device to perform operations comprising:
receiving a request to upload a hearing profile of a user;
uploading the hearing profile of the user to a seat assignment system associated with a venue;
receiving, from the seat assignment system, a customized seating chart comprising a visual representation of at least a portion of seating in the venue determined based, at least in part, upon the hearing profile of the user and sound feedback associated with at least the portion of seating in the venue provided by users while listening to audio outputs at the venue;
presenting, on the display, a graphical user interface that shows the customized seating chart;
selecting, from the customized seating chart, a seat for the user from at least the portion of the seating in the venue;
capturing, by the microphone, audio output at the seat selected for the user;
determining sound feedback associated with the audio output captured by the microphone, wherein the sound feedback associated with the audio output captured by the microphone is representative of sound characteristics of the audio output and takes into account at least one of a characteristic of the microphone that captured the audio output or a location of the microphone in association with the user; and
providing the sound feedback associated with the audio output captured by the microphone to a venue audio system, wherein the venue audio system adjusts the audio output based on the sound feedback associated with the audio output captured by the microphone to personalize the audio output for the user.

9. The computer-readable storage medium of claim 8, wherein the operations further comprise presenting, on the display, a graphical user interface that shows an upload hearing profile option, and wherein receiving the request to upload the hearing profile of the user comprises the upload hearing profile option being selected.

10. The computer-readable storage medium of claim 8, wherein the operations further comprise generating the hearing profile of the user based on at least one of hearing test results from a hearing test performed by a hearing test application of the device or hearing test results imported by the hearing test application from equipment external to the device.

11. The computer-readable storage medium of claim 8, wherein selecting, from the customized seating chart, the seat for the user from at least the portion of the seating in the venue comprises:
receiving selection of an automatic seat selection option provided by the graphical user interface that shows the customized seating chart; and
automatically selecting an available seat from at least the portion of the seating in the customized seating chart as the seat for the user.

12. The computer-readable storage medium of claim 8, wherein selecting, from the customized seating chart, the seat for the user from at least the portion of the seating in the venue comprises receiving manual selection, via a user input, of an available seat from at least the portion of the seating in the customized seating chart as the seat for the user.

13. The computer-readable storage medium of claim 8, wherein the operations further comprise:
presenting, on the display, a manual sound feedback graphical user interface including at least one option associated with a first level of manual sound feedback and at least one option associated with a second level of manual sound feedback, wherein the first level of manual sound feedback and the second level of manual sound feedback are based on knowledge of the user; and
receiving, via the manual sound feedback graphical user interface, at least one of the first level of manual sound feedback or the second level of manual sound feedback.

14. The computer-readable storage medium of claim 13, wherein providing the sound feedback associated with the audio output captured by the microphone to the venue audio system comprises providing the sound feedback associated with the audio output captured by the microphone and the at least one of the first level of manual sound feedback or the second level of manual sound feedback to the venue audio system, and wherein the venue audio system adjusts the audio output based on the sound feedback associated with the audio output captured by the microphone to personalize the audio output for the user comprises the venue audio system adjusting the audio output based on the sound feedback associated with the audio output captured by the microphone and the at least one of the first level of manual sound feedback or the second level of manual sound feedback to personalize the audio output for the user.

15. A method comprising:
receiving, by a device comprising a processor, a microphone, and a display, a request to upload a hearing profile of a user;
uploading, by the device, the hearing profile of the user to a seat assignment system associated with a venue;

receiving, by the device, from the seat assignment system, a customized seating chart comprising a visual representation of at least a portion of seating in the venue determined based, at least in part, upon the hearing profile of the user and sound feedback associated with at least the portion of seating in the venue provided by users while listening to audio outputs at the venue;

presenting, by the device on the display, a graphical user interface that shows the customized seating chart;

selecting, by the device, from the customized seating chart, a seat for the user from at least the portion of the seating in the venue;

capturing, by the microphone, audio output at the seat selected for the user;

determining, by the device, sound feedback associated with the audio output captured by the microphone, wherein the sound feedback associated with the audio output captured by the microphone is representative of sound characteristics of the audio output and takes into account at least one of a characteristic of the microphone that captured the audio output or a location of the microphone in association with the user; and providing, by the device, the sound feedback associated with the audio output captured by the microphone to a venue audio system, wherein the venue audio system adjusts the audio output based on the sound feedback associated with the audio output captured by the microphone to personalize the audio output for the user.

16. The method of claim 15, further comprising generating the hearing profile of the user based on at least one of hearing test results from a hearing test performed by a hearing test application of the device or hearing test results imported by the hearing test application from equipment external to the device.

17. The method of claim 15, wherein selecting, from the customized seating chart, the seat for the user from at least the portion of the seating in the venue comprises:
receiving selection of an automatic seat selection option provided by the graphical user interface that shows the customized seating chart; and
automatically selecting an available seat from at least the portion of the seating in the customized seating chart as the seat for the user.

18. The method of claim 15, wherein selecting, from the customized seating chart, the seat for the user from at least the portion of the seating in the venue comprises receiving manual selection, via a user input, of an available seat from at least the portion of the seating in the customized seating chart as the seat for the user.

19. The method of claim 15, further comprising:
presenting, on the display, a manual sound feedback graphical user interface including at least one option associated with a first level of manual sound feedback and at least one option associated with a second level of manual sound feedback, wherein the first level of manual sound feedback and the second level of manual sound feedback are based on knowledge of the user; and
receiving, via the manual sound feedback graphical user interface, at least one of the first level of manual sound feedback or the second level of manual sound feedback.

20. The method of claim 19, wherein providing the sound feedback associated with the audio output captured by the microphone to the venue audio system comprises providing the sound feedback associated with the audio output captured by the microphone and the at least one of the first level of manual sound feedback or the second level of manual sound feedback to the venue audio system, and wherein the venue audio system adjusts the audio output based on the sound feedback associated with the audio output captured by the microphone to personalize the audio output for the user comprises the venue audio system adjusting the audio output based on the sound feedback associated with the audio output captured by the microphone and the at least one of the first level of manual sound feedback or the second level of manual sound feedback to personalize the audio output for the user.

* * * * *